US012751946B2

(12) United States Patent
Batt

(10) Patent No.: US 12,751,946 B2
(45) Date of Patent: Oct. 6, 2026

(54) TOPICAL ANAESTHETIC COMPOSITION HAVING IMPROVED VASOCONSTRICTOR STABILITY

(71) Applicant: Animal Ethics Pty Ltd, Yarra Glen (AU)

(72) Inventor: Laurie Batt, Auckland (NZ)

(73) Assignee: Animal Ethics Pty Ltd, Yarra Glen (AU)

( * ) Notice: Subject to any disclaimer, the term of this patent is extended or adjusted under 35 U.S.C. 154(b) by 439 days.

(21) Appl. No.: 18/563,351

(22) PCT Filed: Jun. 10, 2022

(86) PCT No.: PCT/AU2022/050576
§ 371 (c)(1),
(2) Date: Nov. 21, 2023

(87) PCT Pub. No.: WO2022/256878
PCT Pub. Date: Dec. 15, 2022

(65) Prior Publication Data

US 2024/0226079 A1 Jul. 11, 2024

(30) Foreign Application Priority Data

Jun. 10, 2021 (AU) ................................ 2021203856

(51) Int. Cl.

| | |
|---|---|
| ***A61K 31/445*** | (2006.01) |
| ***A61K 9/00*** | (2006.01) |
| ***A61K 31/137*** | (2006.01) |
| ***A61K 31/14*** | (2006.01) |
| ***A61K 31/167*** | (2006.01) |
| ***A61K 47/02*** | (2006.01) |
| ***A61K 47/12*** | (2006.01) |
| ***A61K 47/18*** | (2017.01) |
| ***A61K 47/26*** | (2006.01) |
| ***A61K 47/38*** | (2006.01) |
| ***A61P 23/02*** | (2006.01) |

(52) U.S. Cl.
CPC .......... *A61K 31/445* (2013.01); *A61K 9/0014* (2013.01); *A61K 31/137* (2013.01); *A61K 31/14* (2013.01); *A61K 31/167* (2013.01); *A61K 47/02* (2013.01); *A61K 47/12* (2013.01); *A61K 47/183* (2013.01); *A61K 47/26* (2013.01); *A61K 47/38* (2013.01); *A61P 23/02* (2018.01)

(58) Field of Classification Search
CPC .... A61K 31/445; A61K 31/14; A61K 31/167; A61K 47/183; A61K 47/38; A61P 23/02
See application file for complete search history.

(56) References Cited

FOREIGN PATENT DOCUMENTS

| | | |
|---|---|---|
| WO | WO 2006096913 | 9/2006 |
| WO | WO 2006096914 | 9/2006 |
| WO | WO 2010139752 | 12/2010 |
| WO | WO 2014057365 | 4/2014 |
| WO | WO 2019072723 | 4/2019 |
| WO | WO 2020237284 | 12/2020 |
| WO | WO 2020237295 | 12/2020 |
| WO | WO 2020248010 | 12/2020 |

OTHER PUBLICATIONS

Brustugun, J. et al., "Photodestabilization of Epinephrine by Sodium Metabisulfite," in PDA Journal of Pharmaceutical Science and Technology, Mar. 2000, vol. 54, No. 2, pp. 136-143.
Examination Report dated Feb. 16, 2023 in AU Patent Application No. 2021203856, pp. 1-4.
Grubstean, B. et al., "Stabilization of Epinephrine in a Local Anesthetic Injectable Solution Using Reduced Levels of Sodium Metabisulfite and EDTA," in Drug Development and Industrial Pharmacy, 1992, vol. 18, No. 14, pp. 1549-1566.
International Search Report and Written Opinion dated Aug. 12, 2022 in International Patent Application No. PCT/AU2022/050576, pp. 1-10.
Bonhomme, L., et al., "Stability of Epinephrine in Alkalinized Solutions" In Annals of Emergency Medicine, vol. 19, No. 11, Nov. 1, 1990, pp. 1242-1244.
Examination Report dated Dec. 15, 2024 in SA Patent Application No. 523451203, pp. 1-6.
Extended European Search Report dated Jan. 13, 2025 in EP Patent Application No. 22818999.9, pp. 1-11.

*Primary Examiner* — Kamal A Saeed
(74) *Attorney, Agent, or Firm* — Byrne Poh LLP; Nina R. Horan

(57) ABSTRACT

This invention relates to a topical anaesthetic composition having improved adrenaline stability, its method of manufacture, and its use as a topical anaesthetic, particularly in medical applications such as animal husbandry procedures.

18 Claims, 4 Drawing Sheets

TOPICAL ANAESTHETIC COMPOSITION HAVING IMPROVED VASOCONSTRICTOR STABILITY

TECHNICAL FIELD

This invention relates to a topical anaesthetic composition comprising adrenaline. In particular, the invention concerns a topical anaesthetic composition having improved adrenaline stability. However, it will be appreciated that the invention is not limited to this particular field of use.

BACKGROUND ART

The following discussion of the prior art is provided to place the invention in an appropriate technical context and enable the advantages of it to be more fully understood. It should be appreciated, however, that any discussion of the prior art throughout the specification should not be considered as an express or implied admission that such prior art is widely known or forms part of the common general knowledge in the field Tri-Solfen™ is an anaesthetic solution developed by the Australian company Animal Ethics Ltd and is primarily used as a pain relief and wound care product for lambs and calves undergoing surgical husbandry procedures. It is topically applied to a wound to achieve local action at the site of application. The 'original formulation' as used in Australia and New Zealand is shown in Table 1 and has been used to successfully treat over 80 million animals undergoing routine surgeries in the Australian livestock industry.

DISCLOSURE OF INVENTION

The present inventors have discovered that instability of the original Tri-Solfen™ formulation is primarily due to the instability of adrenaline over time. The present inventors have also discovered a way of stabilising adrenaline, which means that a lower concentration of adrenaline can be used relative to the original formulation, and that may overcome the hurdle of not meeting regulatory authority requirements in some jurisdictions.

According to a first aspect of the present invention, there is provided a topical anaesthetic composition (Formulation 1) comprising:

about 5% w/w lignocaine;
about 0.5% w/w bupivacaine;
about 0.5% w/w cetrimide;
about 0.0045% w/w adrenaline;
about 10% w/w liquid sorbitol (70%);
about 0.5% w/w 2-hydroxyethyl cellulose;
about 0.0045% w/w sodium metabisulfite;
about 0.250% w/w citric acid; and
about 0.05% w/w EDTA,
wherein said composition has a final pH of approximately 2.4 to 3.4.

The term "about" as used in relation to the composition means±10% variance, which is inclusive of all values between 1% and 10%, including 1, 1.5, 2, 2.5, 3, 3.5, 4, 4.5, 5, 5.5, 6, 6.5, 7, 7.5, 8, 8.5, 9, 9.5 and 10%.

Preferably the composition is stable for at least 12 months when stored between room temperature and 30° C., wherein room temperature means about 20-22° C. (68-72° F.). "At least about 12 months" includes 12, 13, 14, 15, 16, 17, 18, 19, 20, 21, 22, 23 and 24 months, as well as perhaps additional months but normally less than 36 or 48 months. Preferably the composition is stable for about or for at least about 24 months at room temperature, wherein room temperature means about 20-22° C. (68-72° F.). "At least about 24 months" includes 24, 25, 26, 27, 28, 29 and 30 months, as well as perhaps additional months but normally less than 36 or 48 months.

Preferably the composition is semi viscous. Preferably the composition has a viscosity not more than about 300 cP.

Preferably the composition has a density in the range of about 1.01-1.05 g/mL.

The final pH of approximately 2.4-3.4 includes all numerical values between 2.4 and 3.4, including 2.4, 2.5, 2.6, 2.7, 2.8, 2.9, 3.0, 3.1, 3.2, 3.3 and 3.4. Preferably Formulation 1 has a pH of approximately 2.9±0.1% variance.

It is to be appreciated that, for those ingredients added as salts, there will typically be a dissociation of those salts by solvation in the composition.

TABLE 1

Original Formulation of Tri-Solfen ™ Topical Anaesthetic Solution.

| Ingredient | Function | % w/w |
|---|---|---|
| Lignocaine Hydrochloride Monohydrate | Drug Substance - Anaesthetic | 5.000 |
| Bupivacaine Hydrochloride Monohydrate | Drug Substance- Anaesthetic | 0.500 |
| Cetrimide | Drug Substance- Antiseptic | 0.500 |
| Adrenaline Acid Tartrate | Drug Substance- Vasoconstrictor | 0.00495 |
| Liquid Sorbitol 70% | Humectant/cooling agent | 10.000 |
| 2-Hydroxyethyl Cellulose | Viscosity modifier | 0.500 |
| Sodium Metabisulphite | Antioxidant | 0.150 |
| Brilliant Blue FCF | Marker dye | 0.005 |
| Reverse Osmosis (RO) Water | Solvent | q.s. |

Lignocaine and bupivacaine are utilised as topical anaesthetic agents. Adrenaline is utilised as a vasoconstrictor to increase the anaesthetic effect by reducing blood flow and minimising any systemic distribution of the anaesthetic agents. In addition to topical anaesthesia, other key attributes are: the inclusion of an antiseptic, cetrimide, to minimise infection and promote wound healing; a semi-viscous formulation, to allow efficient dosing via a dosing gun while prolonging contact with the wound; and, the inclusion of a dye, to identify skin contact and spillage.

A disadvantage of the original formulation is that it has a less than optimal stability/shelf life. Another disadvantage of the original formulation is that it cannot be used commercially in some jurisdictions because of the relatively high concentration of adrenaline within the formulation.

It is an object of the present invention to overcome or ameliorate one or more the disadvantages of the prior art, or at least to provide a useful alternative.

Preferably lignocaine is added to the composition in its salt form, such as lignocaine hydrochloride. Preferably the composition provides a dosage strength of about 50 mg/mL lignocaine $HCl \cdot H_2O$.

Preferably bupivacaine is added to the composition in its salt form, such as bupivacaine hydrochloride. Preferably the composition provides a dosage strength of about 5.0 mg/mL bupivacaine $HCl \cdot H_2O$.

Preferably the composition provides a dosage strength of about 5.0 mg/mL cetrimide.

Preferably adrenaline is added to the composition in its salt or ester form, such as adrenaline bitartrate. Adrenaline bitartrate is also known as adrenaline tartrate, adrenaline acid tartrate and epinephrine bitartrate. Preferably the composition provides a dosage strength of about 0.0451 mg/mL adrenaline bitartrate.

Liquid sorbitol (70%) is also known as sorbitol crystallising 70%, sorbitolum, and sorbitol solution.

2-hydroxyethyl cellulose is also known as hydroxyethylcellulose, hydroxyethyl cellulose and Natrosol.

Citric acid is also known as citric acid anhydrous and anhydrous citric acid. Citric acid (anhydrous) is a tricarboxylic acid found in citrus fruits. Citric acid (anhydrous) is not present in the original formulation, but is added to the composition at a level of about 0.250% w/v as a buffer.

Preferably EDTA is added to the composition in its salt form, such as disodium EDTA.

Disodium EDTA is also known as disodium Edetate and Edetate disodium. Disodium EDTA is not present in the original formulation, but is present at a level of 0.050% in the composition to chelate metals ions which contribute to the degradation of adrenaline.

Sodium metabisulphite is included as an antioxidant in the original formulation. It is present at a level of 0.15% in the original formulation, but is reduced to 0.0045% in the composition, in order to reduce degradation of adrenaline through non-oxidative pathways.

Optionally, the composition can further comprise a detectable marker, with a quantity to suit. Any suitable type of detectable marker can be used. The marker may be, for instance, visible to the eye or visible under UV light. The detectable marker is preferably a visual marker and can be visible either before the composition is applied to the subject and/or after the composition is applied to the subject. The detectable marker is preferably a colourant. The colourant can be a pigment and/or dye. Suitable colourants include, for example, common food dyes or the ORCODERM™, ORCOBRITE™ and ORCOFUR™ lines of pigments and dyes sold by the Organic Dyestuffs Corporation. Preferably, the detectable marker is non-toxic and will not permanently stain the skin or animal hide or surrounding hair, fur or wool. The detectable marker can be brilliant blue at a concentration of about 0.005% w/w.

Optionally, the composition can further comprise a pH adjuster, such as an acid or base. Any suitable type of acid or base can be used. The acid can be, for example, sulfuric acid, hydrochloric acid, nitric acid, phosphoric acid, malic acid, malonic acid or carbon dioxide. The base can be, for example, sodium hydroxide, ammonium hydroxide, magnesium hydroxide, triethanolamine or calcium hydroxide. For example, the composition can comprise sodium hydroxide (e.g. 2M solution), with a quantity to suit. For example, the composition can comprise sulphuric (sulfuric) acid (e.g. 30% w/v), with a quantity to suit.

The composition can comprise water, with a quantity sufficient for 100% w/v.

The inventors have found that pH has potential to impact the original formulation in two ways: 1. catalysing degradation of adrenaline; and, 2. impacting viscosity through altering the chemical stability of ethyl hydroxycellulose.

The inventors have found that adrenaline degradation is pH dependent and the risk of pH impacting adrenaline degradation is high.

The inventors have found that viscosity changes occurring during the shelf life have no adverse impact on the spreadability and coating of the composition, and hence the risk of viscosity impacting safety and efficacy is low.

The inventors have found that sodium metabisulphite undergoes other reactions in the composition, in addition to "sacrificial" oxidation to sodium sulfate. These alternate reactions include the formation of adrenaline sulphonate. The inventors have found that as the adrenaline level decreased, and level of adrenaline degradants increases in the presence of higher levels of sodium metabisulphite. Hence, compared with the original formulation, the level of sodium metabisulphite in the composition can be decreased.

According to a second aspect of the present invention, there is provided a topical anaesthetic composition (Formulation 2) comprising:

about 5% w/w lignocaine hydrochloride;
about 0.5% w/w bupivacaine hydrochloride;
about 0.5% w/w cetrimide;
about 0.0045% w/w adrenaline bitartrate;
about 10% w/w liquid sorbitol (70%);
about 0.5% w/w 2-hydroxyethyl cellulose;
about 0.0045% w/w sodium metabisulfite;
about 0.250% w/w citric acid (anhydrous);
about 0.05% w/w disodium EDTA;
optionally, a pH adjuster, with a quantity to suit; and
water, with a quantity to suit,
wherein said composition has a final pH of about 2.9.

The term "about" as used in relation to Formulation 2 means f 10% variance.

Formulation 2 can have features/ingredients as described for Formulation 1, context permitting.

According to a third aspect of the present invention, there is provided a method for anaesthetizing a subject, said method comprising the step of applying topically to the subject the composition according to the first (Formulation 1) or second aspect (Formulation 2) of the present invention.

According to a fourth aspect of the present invention, there is provided the use of the composition according to the first (Formulation 1) or second aspect (Formulation 2) in the preparation of a topical medicament for providing anaesthesia to a subject.

According to a fifth aspect of the present invention, there is provide a method of preparing a topical anaesthetic composition, wherein said method comprises the steps of:

1. combining the following ingredients of Formulation 1 or Formulation 2: water, citric acid, sorbitol, bupivacaine, lignocaine, EDTA, 2-hydroxyethyl cellulose, cetrimide, detectable marker (if any), and sodium metabisulphite;
2. adjusting the pH of the combined ingredients produced in step 1 using a pH adjuster to a pH of approximately 2.4 to 3.4 or 2.9 (if required);
3. adding adrenaline; and
4. adding water, to balance, wherein said composition produced in step 4 has a final pH of approximately 2.4 to 3.4 or 2.9.

Preferably, the ingredients are added in the following order:

1. Water;
2. Citric acid;
3. Sorbitol;
4. Bupivacaine and/or lignocaine;
5. EDTA;
6. 2-hydroxyethyl cellulose;
7. Cetrimide
8. Detectable marker (if required);
9. Sodium metabisulphite;
10. pH adjuster (if required);
11. Adrenaline; and
12. Water, to balance.

Preferably, the composition is used for anaesthetizing an open wound, preferably an open skin wound, such as a laceration, surgical incision, abrasion, ulcer or burn of the subject. Such a wound is likely to actively bleed or weep. However, the composition may be applied to a sutured skin wound and the like—whenever anaesthesia of a skin wound is required.

The subject can be a human. The subject can be another type of mammal or animal. The subject can be a farm animal or livestock, such as a sheep, horse, cow, goat or pig. The subject can be a companion animal, such as a cat or dog. The subject can be a laboratory animal, such as a rodent, mouse, rat or rabbit. Preferably the subject is a human, dog, pig, piglet, horse, sheep, cow, lamb or calf.

The composition can be used for an animal husbandry procedure. The procedure can be, for example, mulesing, shearing, castration, tail docking, ear tagging, ear notching, de-homing, branding, marking, or treating an open wound, e.g. caused by shearing or misadventure.

Preferably, the composition is used for mulesing, castration, tail docking, de-horning, branding or treating an open wound. Preferably, the composition is used for mulesing which is performed so as to prevent flystrike.

The composition can be applied to the subject as a spray-on gel so as to minimise pain related to touching or handling a wound, minimise the risk of infection from skin contamination and so that the wound need not be disturbed more than necessary. Alternatively, the composition can be applied as a gel by hand, or squeezed from a tube to fill a wound caused, say, during a de-homing procedure.

Preferably, the composition is in the form of a sticky, viscous gel. Preferably, the composition is in the form of a spray-on gel that can coat a wound of the subject and can maximise delivery of the active ingredients to the wound by way of staying moist and viscous (i.e. "sticky").

Preferred embodiments of the invention are defined in the paragraphs below. Context permitting, the features of any paragraph may be read in combination with any other paragraph or paragraphs. Likewise, features of a product/composition may be features of a method, and vice-versa. Also, context permitting, the features of any paragraph below may be read in combination with any other paragraph or paragraphs located elsewhere in this specification, particularly the DISCLOSURE OF INVENTION, BEST MODE AND METHOD FOR CARRYING OUT THE INVENTION and the CLAIMS.

1. A topical anaesthetic composition comprising:
about 5% w/w lignocaine;
about 0.5% w/w bupivacaine;
about 0.5% w/w cetrimide;
about 0.0045% w/w adrenaline;
about 10% w/w liquid sorbitol (70%);
about 0.5% w/w 2-hydroxyethyl cellulose;
about 0.0045% w/w sodium metabisulfite;
about 0.250% w/w citric acid; and about 0.05% w/w EDTA,
wherein said composition has a final pH of approximately 2.4 to 3.4.

2. The composition of paragraph 1, wherein said composition has a pH of 2.9 0.1% variance.

3. The composition of paragraph 1 or paragraph 2, wherein said composition comprises a detectable marker, with a quantity to suit.

4. The composition of paragraph 1, 2 or 3, wherein the composition further comprises a pH adjuster.

5. The composition of paragraph 4, wherein the pH adjuster comprises:
an acid such as sulfuric acid, hydrochloric acid, nitric acid, phosphoric acid, malic acid, malonic acid, or carbon dioxide; or
a base such as sodium hydroxide, ammonium hydroxide, magnesium hydroxide, triethanolamine or calcium hydroxide.

6. The composition of any one of the preceding paragraphs, wherein:
the lignocaine is added to the composition as a salt, such as lignocaine hydrochloride;
the bupivacaine is added to the composition as a salt, such as bupivacaine hydrochloride;
the adrenaline is added to the composition as a salt or ester, such as adrenaline bitartrate; and/or
the EDTA is added to the composition as a salt, such as disodium EDTA.

7. A topical anaesthetic composition comprising:
about 5% w/w lignocaine hydrochloride;
about 0.5% w/w bupivacaine hydrochloride;
about 0.5% w/w cetrimide;
about 0.0045% w/w adrenaline bitartrate;
about 10% w/w liquid sorbitol (70%);
about 0.5% w/w 2-hydroxyethyl cellulose;
about 0.0045% w/w sodium metabisulfite;
about 0.250% w/w citric acid (anhydrous);
about 0.05% w/w disodium EDTA;
optionally, a pH adjuster, with a quantity to suit; and
water, with a quantity to suit,
wherein said composition has a final pH of about 2.9.

8. The composition of any one of the preceding paragraphs, wherein the composition has:
a viscosity not more than about 300 cP; and/or
a density in the range of about 1.01-1.05 g/mL.

9. The composition of any one of the preceding paragraphs, wherein: the composition is stable for at least 12 months when stored between about 20° C. and about 30° C.;
the composition is stable for at least 18 months when stored between about 20° C. and about 30° C.; or
the composition is stable for at least 24 months when stored between about 20° C. and about 30° C.

10. The composition of any one of the preceding paragraphs, wherein:
the composition is in the form of a sticky, viscous gel;
the composition is in the form of a sprayable gel;
the composition is in the form of a gel that can be squeezed or dispensed from a tube; or
the composition is in the form of a spray-on gel that can coat a wound of the subject and can maximise delivery of active ingredients to the wound by way of staying moist, viscous and sticky.

11. A method for anaesthetizing a subject, said method comprising the step of applying topically to the subject the composition according to any one of paragraphs 1 to 10.

12. Use of the composition according to any one of paragraphs 1 to 10 in the preparation of a topical medicament for providing anaesthesia to a subject.

13. The method of paragraph 11 or the use of paragraph 12, wherein the composition is used for anaesthetizing an open wound or a sutured skin wound.

14. The method of paragraph 11 or 13, or the use of paragraph 12 or 13, wherein the subject is undergoing or is to undergo an animal husbandry procedure or surgical procedure.

15. The method of paragraph 14 or the use of paragraph 14, wherein procedure is mulesing, shearing, castration, tail docking, ear tagging, ear notching, de-horning, branding, marking, or treating an open wound such as caused by shearing, misadventure or surgical incision.

16. A method of mulesing, shearing, castrating, tail docking, ear tagging, ear notching, de-horning, branding or marking a subject, or treating an open wound of a subject such as caused by shearing, misadventure or surgical incision, said method comprising the step of applying topically to the subject the composition according to any one of paragraphs 1 to 10; or use of the composition according to any one of paragraphs 1 to 10 in the preparation of a topical medicament for mulesing, shearing, castrating, tail docking, ear tagging, ear notching, de-homing, branding or marking a subject, or treating an open wound of a subject such as caused by shearing, misadventure or surgical incision.

17. The method of paragraph 11, 13, 14, 15 or 16, or the use of paragraph 12, 13, 14, 15 or 16, wherein:

the subject is a non-human animal;

the subject is a mammal;

the subject is a farm animal or livestock, such as such as a sheep, horse, cow, goat or pig;

the subject is a companion animal, such as a cat or dog;

the subject is a laboratory animal, such as a rabbit, rodent, mouse, rat, hamster, gerbil or guinea pig; or the subject is a dog, pig, piglet, horse, sheep, cow, lamb or calf.

18. The method of paragraph 11, 13, 14, 15 or 16, or the use of paragraph 12, 13, 14, 15 or 16, wherein the subject is a human.

19. A method of preparing the topical anaesthetic composition of any one of paragraphs 1 to 10, wherein said method comprises the steps of:

1. combining the following ingredients: water, citric acid, sorbitol, bupivacaine, lignocaine, EDTA, 2-hydroxyethyl cellulose, cetrimide, detectable marker (if any), and sodium metabisulphite;
2. adjusting the pH of the combined ingredients produced in step 1 using a pH adjuster to a pH of approximately 2.4 to 3.4 or 2.9 (if required);
3. adding adrenaline; and
4. adding water, to balance, wherein said composition produced by step 4 has a final pH of approximately 2.4 to 3.4 or 2.9.

20. The method of paragraph 19, wherein the ingredients are added in the following order:

1. Water;
2. Citric acid;
3. Sorbitol;
4. Bupivacaine and/or lignocaine;
5. EDTA;
6.2-Hydroxyethyl cellulose;
7. Cetrimide
8. Detectable marker (if any);
9. Sodium metabisulphite;
10. pH adjuster (if required);
11. Adrenaline; and
12. Water, to balance.

Having broadly described the invention in its various embodiments, non-limiting examples of embodiments will now be given.

BEST MODE AND METHOD FOR CARRYING OUT THE INVENTION

Figure 1:
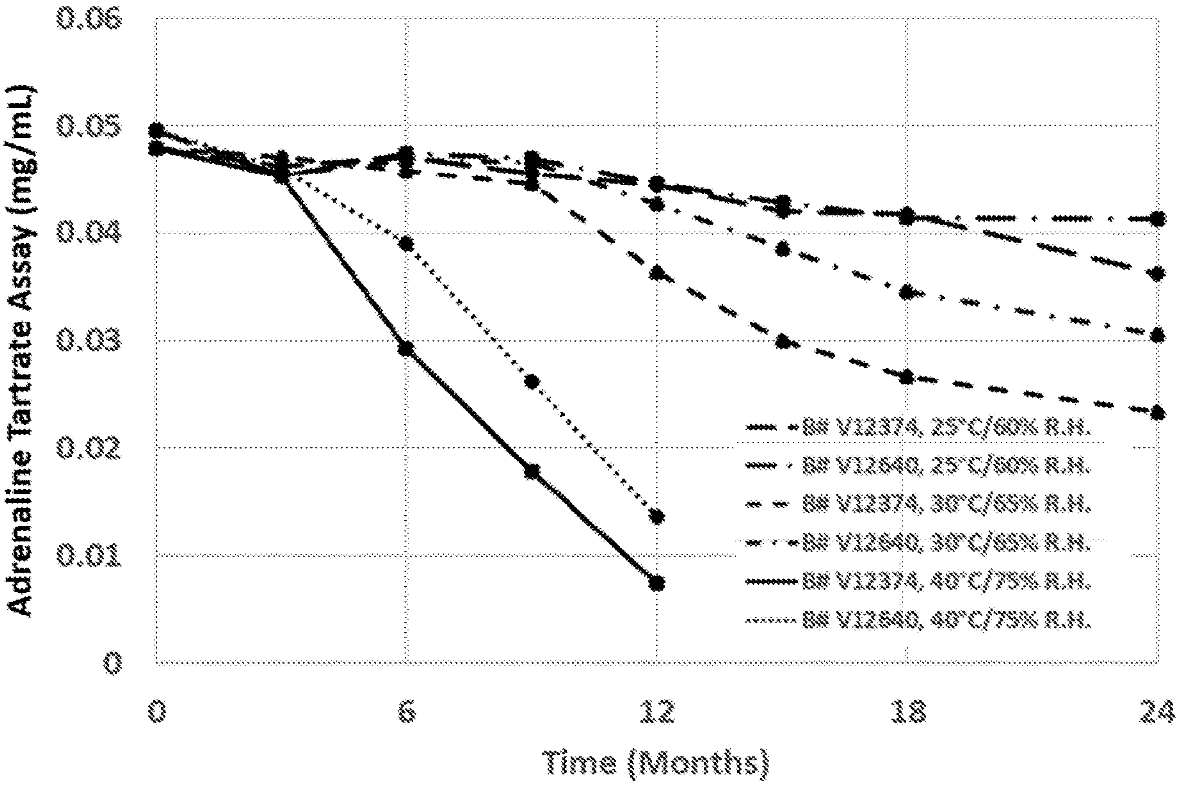
FIG. 1. Adrenaline assay on stability of the original formulation of Table 1.

Example 1—Assay Stability Results of the Original Formulation

The development of the original formulation of Tri-Solfen™ topical solution began in Australia in response to the absence of a registered and widely available product to provide pain relief following mulesing in lambs. The original formulation is shown in Table 1. Table 2 below presents a summary of assay stability results of the original formulation.

TABLE 2

Summary of Assay Results on Stability - 'Original Formulation'.

| Batch# | Assay (g/L) | Months 0 | 3 | 6 | 9 | 12 | 15 | 18 | 24 | Max % Decrease in Assay wrt Time Zer |
|---|---|---|---|---|---|---|---|---|---|---|
| Long Term: 25° C./60% R.H. | | | | | | | | | | |
| V12374 | Lignocaine HCl•$H_2O$ | 49.9 | 50.7 | 50.8 | 50.1 | 50.3 | 50.2 | 50.1 | 50.9 | NA |
| | Bupivacaine HCl•$H_2O$ | 5.00 | 5.13 | 5.08 | 5.09 | 5.08 | 5.09 | 5.04 | 4.89 | 2.2 |

TABLE 2-continued

Summary of Assay Results on Stability - 'Original Formulation'.

| Batch# | Assay (g/L) | Months 0 | 3 | 6 | 9 | 12 | 15 | 18 | 24 | Max % Decrease in Assay wrt Time Zer |
|---|---|---|---|---|---|---|---|---|---|---|
| | Cetrimide | 4.98 | 4.98 | 4.97 | 4.97 | 4.96 | 4.96 | 4.98 | 4.98 | 0.4 |
| | Adrenaline Bitartrate | 0.0479 | 0.0462 | 0.0470 | **0.0455** | **0.0445** | **0.0420** | **0.0417** | *0.0362* | 24.4 |
| V12640 | Lignocaine $HCl{\bullet}H_2O$ | 51.1 | 50.4 | 50.4 | 50.5 | 49.7 | 49.8 | 50.6 | 50.8 | 2.5 |
| | Bupivacaine $HCl{\bullet}H_2O$ | 5.12 | 5.10 | 5.06 | 5.14 | 5.04 | 5.07 | 5.11 | **4.86** | **5.1** |
| | Cetrimide | 5.00 | 4.98 | 4.97 | 4.99 | 4.97 | 4.99 | 4.98 | 4.91 | 0.6 |
| | Adrenaline Bitartrate | 0.0495 | 0.0453 | 0.0474 | **0.0469** | **0.0446** | **0.0428** | **0.0414** | **0.0413** | **16.6** |
| Intermediate: 30° C./65% R.H. | | | | | | | | | | |
| V12374 | Lignocaine $HCl{\bullet}H_2O$ | 49.9 | 50.4 | 51.0 | 50.3 | 49.9. | 50.0 | 50.7 | 50.7 | NA |
| | Bupivacaine $HCl{\bullet}H_2O$ | 5.00 | 5.14 | 5.12 | 5.12 | 5.05 | 5.07 | 5.12 | 4.87 | 2.6 |
| | Cetrimide | 4.98 | 5.06 | 4.99 | 4.99 | 4.99 | 5.00 | 5.02 | 4.89 | 1.8 |
| | Adrenaline Bitartrate | 0.0479 | 0.0471 | 0.0458 | **0.0446** | *0.0363* | *0.0300* | *0.0267* | *0.0234* | *51.1* |
| V12640 | Lignocaine $HCl{\bullet}H_2O$ | 51.1 | 50.7 | 50.7 | 50.4 | 50.0 | 49.6 | 50.6 | 50.7 | 2.9 |
| | Bupivacaine $HCl{\bullet}H_2O$ | 5.12 | 5.13 | 5.09 | 5.14 | 5.06 | 5.05 | 5.09 | 4.86 | 5.1 |
| | Cetrimide | 5.00 | 5.01 | 4.96 | 4.99 | 4.99 | 4.98 | 4.98 | 4.87 | 2.6 |
| | Adrenaline Bitartrate | 0.0495 | **0.0454** | **0.0468** | **0.0466** | *0.0427* | *0.0386* | *0.0345* | *0.0306* | *38.2* |
| Intermediate: 40° C./75% R.H. | | | | | | | | | | |
| V12374 | Lignocaine $HCl{\bullet}H_2O$ | 49.9 | 50.4 | 50.5 | 49.8 | 50.1 | | Not Tested | | 0.2 |
| | Bupivacaine $HCl{\bullet}H_2O$ | 5.00 | 5.09 | 5.06 | 5.06 | 5.07 | | | | NA |
| | Cetrimide | 4.98 | 4.97 | 4.99 | 4.94 | 4.91 | | | | 1.4 |
| | Adrenaline Bitartrate | 0.0479 | **0.0453** | *0.0293* | *0.0178* | *0.00738* | | | | *84.6* |
| V12640 | Lignocaine $HCl{\bullet}H_2O$ | 51.1 | 50.7 | 50.2 | 50.0 | 50.0 | | | | 2.2 |
| | Bupivacaine $HCl{\bullet}H_2O$ | 5.12 | 5.14 | 5.06 | 5.10 | 5.06 | | | | 1.2 |
| | Cetrimide | 5.00 | 5.00 | 4.96 | **4.63** | 4.99 | | | | **7.4** |
| | Adrenaline Bitartrate | 0.0495 | **0.0460** | *0.0390* | *0.0262* | *0.0136* | | | | 72.5 |

Accelerated: 40° C./75% R.H.
NA: Not Applicable. No assay values at subsequent time points were less than the time zero assay.
Bolded Text Significant decrease in assay (i.e. a 5% decrease or more)
Italicized Text Out of specification Significant decreases in assay (i.e. a decrease of 5% or greater) are highlighted in yellow and out of specification (OOS) results are highlighted in orange.

The final column of Table 2 gives the largest decrease in assay observed on stability and Table 3 summarises information relating to the significant decreases in assay.

TABLE 3

Significant Changes in Assay - Original Formulation.

| Batch # | Analyte | Time Point | Condition | Assay Decrease (%) | Comment |
|---|---|---|---|---|---|
| V12640 | Bupivacaine $HCl{\bullet}H_2O$ | 24 M | 25 °C/60% R.H | 5.1% | Not attributable to degradation because; No consistent trend of the assay |
| V12640 | Bupivacaine $HCl{\bullet}H_2O$ | 24 M | 30 °C/65% R.H | 5.1% | decreasing with time Decrease in assay was not larger with greater stress |

TABLE 3-continued

| Significant Changes in Assay - Original Formulation. | | | | | |
|---|---|---|---|---|---|
| Batch # | Analyte | Time Point | Condition | Assay Decrease (%) | Comment |
| | | | | | No corresponding decrease was observed in B# 12374 |
| V12640 | Cetrimide | 9 M | 40 °C/75% R.H | 7.4% | Not attributable to degradation because; |
| | | | | | No consistent trend with time |
| | | | | | No corresponding decrease was observed in B# 12374 |
| V12374 | Adrenaline | 24 M | 25 °C/60% R.H | 24.4% | Attributed to degradation because; |
| | | 24 M | 30 °C/65% R.H | 51.1% | Assay decreased consistently with time |
| | | 12 M | 40 °C/75% R.H | 84.6% | Decrease in assay was larger with greater |
| V12640 | | 24 M | 25 °C/60% R.H | 16.6% | stress |
| | | 24 M | 30 °C/65% R.H | 38.2% | Decrease was consistently observed in |
| | | 12 M | 40 °C/75% R.H | 72.5% | both batches |

This stability data demonstrates that, while significant changes were observed for bupivacaine HCl·$H_2O$ and cetrimide in the original formulation, these changes are not attributable to degradation of these drug substances, and that the assays remained with specification. In marked contrast, the stability data clearly demonstrates the instability of adrenaline in the original formulation.

The instability of adrenaline relative to cetrimide is clear in stability data for the original formulation (Table 2), such that a 10% overage of adrenaline is applied in the formulation. With the exception of an out of trend (OOT) assay drop of 7.4% at 9 months 40° C./75% R.H. (refer to comment in Table 3) cetrimide assays showed the least change (other than the OOT result, the largest assay drop was 1.8%, which is within expected levels of analytical variability) whereas adrenaline assays showed the greatest change (with a 72.4% drop observed at 12 months, 40° C./75% R.H).

This instability is evident in the original formulation, where the assay of adrenaline decreases with time and thermal stress (Table 2; FIG. 1), such that a 10% overage of adrenaline is applied to the original formulation and the product label stipulates that storage temperatures may not exceed 30° C. (Australia) or 25° C. (New Zealand).

Based on these results, stabilisation of adrenaline, by minimising the degradation pathways, was the principal goal of the present inventors' refinement of the original formulation. The other three drug substances in the original formulation are stable; there is no trend of a decreasing lignocaine, bupivacaine or cetrimide assay with time in stability studies conducted on the original formulation up to 12 months under accelerated conditions, and up to 24 months under long-term and intermediate conditions (Table 2).

FIG. 1 represents a plot of the adrenaline assay on stability, which demonstrates the marked decrease in adrenaline stability in the original formulation under accelerated conditions, relative to long term and intermediate conditions. The temperature dependence of adrenaline degradation is reflected by the original formulation's product label, which requires storage below 30° C. (Australia) and 25° C. (New Zealand). This instability of adrenaline is also compensated for by a 10% overage.

Freeze/thaw temperature cycling studies and photostability studies were not conducted in development of the original formulation. Consequently, the storage conditions for the original formulation product in Australia are "Store below 30° C. (room temperature). Do not store at low temperature. Protect from light."

Degradation of lignocaine, bupivacaine and cetrimide was only observed to occur in response to the deliberately extreme chemical stressors applied in formed degradation studies (not shown).

Table 4 summarises information on the relative chemical stability of the drug substances, obtained in forced degradation studies. In these studies, the duration of exposure to stress applied to adrenaline was far less than applied to the other drug substances (i.e. the period of exposure to thermal and chemical stress was far shorter, and amount of light exposure was far lower). Despite the significantly lower exposure of adrenaline to the various stressors, the % degradation of adrenaline was significantly greater than observed for the three other drug substances, with the exception of reductive stress. For samples exposed to reductant, cetrimide showed slightly greater degradation than adrenaline (i.e. 8.4% degradation of cetrimide and 6.4% degradation of adrenaline). However, it is noted that the slightly greater degradation of cetrimide occurred in response to ~4 times longer exposure to the reductant. Consequently, forced degradation data support that adrenaline is the least stable of the four drug substances, with a greater propensity to degrade in response to heat, oxidative, reductive, acid, base and light stress.

TABLE 4

Comparision of Degradation of Drug Substances in Response to Forced Degradation.

| Stress | Duration/Exposure: Adrenaline | Duration/Exposure: Lignocaine, Bupivacaine & Cetrimide | % Degradation: Adrenaline | Lignocaine | Bupivacaine | Cetrimide |
|---|---|---|---|---|---|---|
| Heat | 15 Days | 8 Weeks | 2.5 | 1.1 | 1.5 | 0.5 |
| Oxidation 1 | 15 Days | 8 Weeks | 4.6 | −0.2 | 0.2 | −0.2 |
| Oxidation 2 | 1 Day | 8 Weeks | 70.3 | 3.3 | 5.4 | 1.0 |
| Reduction | 15 Days | 8 Weeks | 6.4 | −0.3 | 0.5 | 8.4 |
| Acid | 15 Days | 8 Weeks | 8.6 | −0.3 | 0.8 | 0.4 |
| Base | 1 Day | 8 Weeks | 73.1 | 1.1 | 0.1 | 0.9 |
| Light | $0.9 \times 10^6$ lux hrs | $51 \times 10^6$ lux hrs | 51.6 | 9.9 | 11.2 | 8.9 |

The relatively facile degradation of adrenaline in response to a wide range of stressors (i.e. acid, base, oxidation, reduction, heat and light) means that adrenaline is the stability-determining component of the original formulation.

Furthermore, excipient compatibility was assessed from drug product stability data (not shown) which demonstrates instability of adrenaline in the original formulation. Incompatibility between sodium metabisulphite and adrenaline is known, and is evident in the formation of adrenaline sulphonate in the drug product. As the central goal of formulation development was to reduce the rate degradation of adrenaline, one of the strategies investigated to achieve this was to reduce the concentration of sodium metabisulphite.

Example 2—Formulation Development

As noted above, the present inventors have carried out formulation development studies to modify the original formulation of Tri-Solfen™ topical solution to improve the stability of adrenaline, such that an adrenaline overage is no longer required and the product is suitable for registration in markets other than Australia and New Zealand. This optimisation was to be achieved with minimal change to the original formulation, so that clinical and commercial experience with the original formulation was also applicable to the optimised formulation. Achieving this was not straightforward. However, three formulation variables were investigated, to achieve this goal:

- Buffering the drug product. Adrenaline degradation is pH dependent, proceeding via both acid and base-catalysed degradation pathways. Consequently, introduction of a buffer and adjustment of pH into a target region has potential to minimise adrenaline degradation, and favour formation of d-adrenaline over formation of adrenaline degradants.
- Reducing the level of sodium metabisulphite. Sulphonation of adrenaline by sodium metabisulphite is a known incompatibility between the drug substance and the antioxidant. Sodium metabisulphite is present in excess in the original formulation, consequently, reducing the concentration of sodium metabisulphite has potential to reduce adrenaline degradation through sulphonation, without adversely impacting antioxidant performance.
- Addition of EDTA. Degradation of adrenaline is catalysed by metal ions. Consequently, introduction of EDTA to chelate metals ions has potential to reduce adrenaline degradation.

Alternate product development strategies were also investigated, such as replacement of lignocaine with tetracaine, use of alternate antioxidants (butylated hydroxyanisole, menthol, thymol), alternate viscosity modifiers (poloxamer, chitosan), increased levels of the existing viscosity modifier (2-ethyl hydroxycellulose) and use of alternate bases for pH adjustment (triethanolamine). These product development activities are not detailed as they led to dead ends, although they did contribute to the formulation development by ruling out strategies, to stabilise adrenaline, that were initially regarded as promising.

Formulation Development Studies—Investigation of Buffer Level/pH on Viscosity and Chemical Stability of Adrenaline As noted above, formulation refinement was undertaken to improve the stability of adrenaline and included investigation of the impact of buffer level/pH on adrenaline stability. A series of seven 500 mL trial formulations (summarised in Table 5) were prepared with constant levels of lignocaine, bupivacaine, cetrimide, liquid sorbitol 70%, EDTA and Brilliant Blue. Six of the formulations included adrenaline and sodium metabisulphate in a constant 1:1 ratio (w:w), and one formulation contained an increased level of 2-ethyl hydroxycellulose. Citric acid content was varied (0.00% to 0.50%) to investigate the impact of pH changes on chemical stability and viscosity. The pH of the formulations is also included in Table 5.

TABLE 5

Formulations Investigating the Effect of Buffer Level/pH on Adrenaline Stability and Viscosity.

| | Batch # 180710-1* | 180711-2 | 180711-3 | 180711-4 % w/v | 180711-5 | 180711-6 | 180711-7 |
|---|---|---|---|---|---|---|---|
| Lignocaine $HCl \cdot H_2O$ | | | | 5.000 | | | |
| Bupivacaine $HCl \cdot H_2O$ | | | | 0.500 | | | |
| Cetrimide | | | | 0.500 | | | |
| Liquid Sorbitol 70% | | | | 10.000 | | | |
| Disodium EDTA | | | | 0.050 | | | |
| Brilliant Blue | | | | 0.005 | | | |

TABLE 5-continued

Formulations Investigating the Effect of Buffer Level/pH on Adrenaline Stability and Viscosity.

| | Batch # | | | | | | |
|---|---|---|---|---|---|---|---|
| | 180710-1* | 180711-2 | 180711-3 | 180711-4 % w/v | 180711-5 | 180711-6 | 180711-7 |
| 2-Hydroxyethyl Cellulose | | | | 0.500% | | | 0.75% |
| Citric Acid (Anhydrous) | 0.000 | 0.000 | 0.52% | 0.251% | 0.105% | 0.505% | 0.504% |
| Sodium Metabisulphite | 0.000 | | | 0.005% | | | |
| Adrenaline Bitartrate | 0.000 | | | 0.005% | | | |
| pH | 4.50 | 4.50 | 2.32 | 3.21 | 3.30 | 2.32 | 2.32 |

*Batch 180710-1 was used as a stock solution to prepare batches 180711-2 to 180711-7, by addition of varying quantities of citric acid, sodium metabisulphite and adrenaline bitartrate, and also 2-hydroxyethel cellulose (B#180711-7).

Table 6 summarises viscosity data, the change in adrenaline assay (with respect to time zero) and adrenaline degradation products (total degradation products and largest individual degradant) on storage of batches 180711-2 to 180711-7 at 50° C., 40° C./75% R.H. and 25° C./60% R.H in 100 mL glass bottles. The batches are presented in order of decreasing pH, from left to right.

TABLE 6

Summary of Viscosity, Change in Adrenaline Assay and Adrenaline Degradation Products, in Formulations of Varying Buffer Leve/pH.

| | | Batch # | | | | | |
|---|---|---|---|---|---|---|---|
| | | 180711-2 | 180711-5 | 180711-4 | 180711-3 pH | 180711-6 | 180711-7 |
| | | 4.50 | 3.30 | 3.21 | 2.32 | 2.32 | 2.32 |
| Viscosity (cP) | T = 0 | 53 | 67 | 83 | 58 | 91 | 487 |
| | 1M 50 °C | 47 | 13 | 29 | 7 | 12 | 34 |
| | 1M 40 °C/75% R.H. | 53 | 47 | 69 | 32 | 54 | 256 |
| Change in Adrenaline | 2M 50 °C | −25.8 | −8.6 | −7.6 | −8.4 | −6.7 | −32.9 |
| Assay (%) Relative to | 2M 40 °C/75% R.H. | −15.5 | −3.8 | −5.7 | −5.3 | −3.8 | −14.1 |
| T = 0. | 2M 25 °C/60% R.H. | −6.5 | −2.5 | −4.0 | −3.1 | 0.3 | −8.4 |
| Adrenaline Degradation | T = 0 | 0.3 | 0.1 | 0.1 | 0.1 | 0.2 | 0.0 |
| Products (Total, %) | 2M 50 °C | 15.1 | 1.7 | 0.7 | 4.0 | 3.4 | 15.0 |
| | 2M 40 °C/75% R.H. | 10.8 | 1.0 | 1.3 | 1.7 | 2.2 | 7.8 |
| | 2M 25 °C/60% R.H. | 3.4 | 0.2 | 0.2 | 0.4 | 0.5 | 1.3 |
| Adrenaline Degradation | T = 0 | 0.2 | 0.1 | 0.1 | 0.1 | 0.2 | 0.0 |
| Products (Largest | 2M 50 °C | 10.4 | 1.7 | 0.7 | 2.8 | 3.4 | 11.6 |
| Individual, %) | 2M 40 °C/75% R.H. | 7.2 | 1.0 | 0.5 | 1.7 | 2.2 | 5.7 |
| | 2M 25 °C/60% R.H. | 2.3 | 0.2 | 0.2 | 0.4 | 0.5 | 0.8 |

Observations relating to viscosity:

A decrease in viscosity was observed for all batches stored for 1 month at 50° C., with the exception of batch #180711-2, which had the highest pH of 4.5. This drop in viscosity increased with decreasing pH, which is consistent with hydrolysis of 2-hydroxyethyl cellulose.

No consistent/significant decrease in viscosity was observed for all batches stored for 1 month at 40° C./75% R.H.

Observations relating to adrenaline stability:

A temperature dependent decrease in adrenaline assay was observed for all batches and all stability conditions (with the exception of B #180711-6, 2 months long term conditions).

The decrease in assay was much larger for the unbuffered B #180711-2 (which had the highest pH of 4.5) relative to B #s 180711-3 to 180711-6 (which contained varying amounts of citric acid and had pHs ranging between 3.3 and 2.3).

An increase in adrenaline degradation products accompanied the decrease in adrenaline assay.

Adrenaline degradation increased in the presence of a higher level of 2-hydroxyethyl cellulose.

This investigation identified that buffer level/pH impacts the stability of viscosity and adrenaline with opposing pH effects (i.e. viscosity is stabilised with increasing pH and adrenaline is stabilised with decreasing pH) within the pH range investigated. Consequently, a target pH of 2.9 is proposed for the final formulation, to balance these conflicting stability dependencies.

Formulation Development—Investigation of the Ratio of Adrenaline to Sodium Metabisulphite Further formulation trials were conducted which investigated the effect of the ratio of adrenaline bitartrate to sodium metabisulphite (in the range of 1:1 to 1:5) on adrenaline stability, in addition to investigating pH variations bracketing the proposed target pH. The formulations were prepared from a 30 L stock solution described in Table 7, with subsequent addition of adrenaline bitartrate (to obtain a concentration of approximately 0.0045% adrenaline bitartrate), sodium metabisulphite (to obtain concentrations in ratios ranging from 1:1 to 1:5, with respect to adrenaline bitartrate) and adjusting to varying pH values.

TABLE 7

| Composition of 30 L Stock Solution | |
|---|---|
| Components | % w/w |
| Lignocaine HCl•$H_2O$ | 5 |
| Bupivacaine HCl•$H_2O$ | 0.5 |
| Cetrimide | 0.5 |
| Liquid Sorbitol 70% | 10 |
| 2-Hydroxyethyl Cellulose | 0.5 |
| Anhydrous Citric Acid | 0.25 |
| EDTA | 0.05 |
| Brilliant Blue FCF | 0.005 |
| Purified Water | q.s. |

The formulations were stored at 40° C./75% R.H. in 1 L Hyperier HDPE barrier packs. Tables 8 to 11 present data for batches adjusted to pH ranging from pH 3.3 (Table 8) to pH 2.7 (Table 11) with data at the target pH of the proposed formulation (pH 2.9) presented in Table 10. Each table summarises data on the stability of adrenaline (decrease in adrenaline assay and largest individual impurity).

TABLE 8

Summary of Change in Adrenaline Assay, Largest Adrenaline Degradation Products and Ratio of d-Adrenaline, in Formulations of Varying Ratios of Adrenaline to Sodium Metabisulphite, pH 3.3.

| Batch # | | 181107-1-4 | 181107-1-5 |
|---|---|---|---|
| pH | | 3.3 | 3.3 |
| Ratio of Adrenaline Bitartrate to Sodium Metabisulphite (w:w) | | 1:1 | 1:3 |
| Decrease in Adrenaline Assay (% LC) Relative to T = 0 | 1M 40 °C/75% R.H. | 1.6 | 1.9 |
| | 2M 40 °C/75% R.H. | 3.7 | 6.3 |
| Adrenaline Degradation Products (Largest Deg (%)) | 1M 40 °C/75% R.H. | 0.505 | 1.345 |
| | 2M 40 °C/75% R.H. | 1.372 | 3.560 |
| Ratio of d-Adrenaline | 2M 40 °C/75% R.H. | 1.68 | 1.25 |

TABLE 9

Summary of Change in Adrenaline Assay, Largest Adrenaline Degradation Products and Ratio of d-Adrenaline, in Formulations of Varying Ratios of Adrenaline to Sodium Metabisulphite, pH 3.1.

| Batch # | | 181107-1-1 | 181107-1-2 | 181107-1-3 |
|---|---|---|---|---|
| pH | | 3.1 | 3.1 | 3.1 |
| Ratio of Adrenaline Bitartrate to Sodium Metabisulphite (w:w) | | 1:1 | 1:3 | 1:5 |
| Decrease in Adrenaline Assay | 1M 40 °C/75% R.H. | 0.3 | 3.9 | 2.6 |
| Relative (% LC) to T = 0 | 2M 40 °C/75% R.H. | 2.0 | 5.6 | 5.8 |
| Adrenaline Degradation | 1M 40 °C/75% R.H. | 0.492 | 0.653 | 0.961 |
| Products (Largest Deg (%)) | 2M 40 °C/75% R.H. | 1.217 | 1.311 | 2.552 |
| Ratio of d-Adrenaline | 2M 40 °C/75% R.H. | 2.56 | 2.57 | 2.54 |

TABLE 10

Summary of Change in Adrenaline Assay, Largest Adrenaline Degradation Products and Ratio of d-Adrenaline, in Formulations of Varying Ratios of Adrenaline to Sodium Metabisulphite, pH 2.9.

| Batch # | | 181107-1-6 | 181107-1-7 | 181107-1-8 |
|---|---|---|---|---|
| pH | | 2.9 | 2.9 | 2.9 |
| Ratio of Adrenaline Bitartrate to Sodium Metabisulphite (w:w) | | 1:1 | 1:3 | 1:5 |
| Decrease in Adrenaline Assay | 1M 40 °C/75% R.H. | 1.0 | 2.0 | 2.4 |
| Relative (% LC) to T = 0 | 2M 40 °C/75% R.H. | 3.1 | 3.7 | 4.8 |
| Adrenaline Degradation | 3M 40 °C/75% R.H. | 3.3 | NT | NT |
| Products (Largest Deg (%)) | 1M 40 °C/75% R.H. | 0.108 | 0.414 | 0.647 |
| Ratio of d-Adrenaline | 2M 40 °C/75% R.H. | 0.434 | 1.031 | 1.537 |
| | 3M 40 °C/75% R.H. | 0.313 | NT | NT |
| Ratio of d-Adrenaline | 2M 40 °C/75% R.H. | 4.84 | 5.14 | 5.25 |
| | 3M 40 °C/75% R.H. | 8.02 | NT | NT |

NT = Not tested

TABLE 11

Summary of Change in Adrenaline Assay Largest Adrenaline Degradation Products and Ratio of d-Adrenaline, in Formulations of Varying Ratios of Adrenaline to Sodium Metabisulphite, pH 2.7.

| | | Batch # | | | | |
|---|---|---|---|---|---|---|
| | | 181107-1-9 | 181107-1-10 | 181107-1-11 | 181107-1-12 | 181107-1-13 |
| | | pH | | | | |
| | | 2.7 | 2.7 | 2.7 | 2.7 | 2.7 |
| | | Ratio of Adrenaline Bitartrate to Sodium Metabisulphite (w:w) | | | | |
| | | 1:1 | 1:2 | 1:3 | 1.4 | 1.5 |
| Decrease in Adrenaline Assay (% LC) Relative to T = 0 | 1 M 40 °C/ 75% R.H. | 5.3 | 1.7 | 1.7 | 1.3 | 1.7 |
| | 2 M 40 °C/ 75% R.H. | 6.2 | 3.3 | 3.2 | 4.0 | 4.3 |
| | 3 M 40 °C/ 75% R.H. | 6.5 | NT | 2.7 | NT | 4.2 |
| Adrenaline Degradation Products (Largest Deg (%)) | 1 M 40 °C/ 75% R.H. | 0.073 | 0.137 | 0.234 | 0.350 | 0.423 |
| | 2 M 40 °C/ 75% R.H. | 0.189 | 0.386 | 0.677 | 0.882 | 0.976 |
| | 3 M 40 °C/ 75% R.H. | 0.110 | NT | 0.663 | NT | 1.18 |
| Ratio of d-Adrenaline | 2 M 40 °C/ 75% R.H. | 8.40 | 8.44 | 8.38 | 8.11 | 8.46 |
| | 3 M 40 °C/ 75% R.H. | 13.54 | NT | 12.98 | NT | 13.66 |

This data demonstrates that adrenaline degradation increased with increasing ratio of sodium metabisulphate, at all pHs investigated. The one exception to this trend is the assay decrease observed at pH 2.7 (Table 11), where a larger assay drop was seen in batch 181107-1-9 (prepared with a 1:1 ratio of adrenaline tartrate:sodium metabisulphite) relative to batches with higher ratios of the antioxidant (i.e. batches 181107-1-10 to 181107-10-13). Inspection of the data indicates that this out-of-trend (OOT) result is due an OOT high assay of batch 181107-1-9 at time zero.

The % of largest individual degradant also increased with increasing ratio of sodium metabisulfite to adrenaline, whereas the ratio of d-adrenaline (relative to 1-adrenaline) was unaffected by changes in the ratio of sodium metabisulphite. The level of d-adrenaline increased with decreasing pH.

This data supports that adrenaline was most stable with a 1:1 ratio of adrenaline bitartrate:sodium metabisulphite. Consequently, a 1:1 ratio of adrenaline bitartrate to sodium metabisulphite is proposed for the final formulation. (i.e. both formulation components present at 0.0045% w/v).

Batch 181107-6 has the composition of the proposed formulation (i.e. a pH of 2.9 and an adrenaline:sodium metabisulphite ratio of 1:1).

Formulation Development Conclusions

The formulation development studies summarised above identified the following changes to the original formulation, to improve the stability of adrenaline and leading to the proposed formulation:

Introduce citric acid buffer to control pH to a target of pH 2.9. This is achieved through addition of citric acid anhydrous at a level of 0.250% (w/w) and adjusting the formulation to pH 2.9 with sodium hydroxide (2 M) or sulphuric acid (30%).

Reduce the level of sodium metabisulphite from 0.15% (w/w) to 0.0045% (w/w).

Introduce disodium EDTA at a level of 0.050% (w/w).

Example 3—Medium and High Risk Assessment

Formulation variables with a medium or high risk to impact the drug product critical quality attributes (CQAs)—i.e. buffer level/pH and sodium metabisulphite levels—were investigated further, as summarised below.

The original formulation of Tri-Solfen™ topical solution is a true solution, with all components present at levels below their solubility limits and fully dissolved in the solvent, water. Consequently, the manufacturing process involves a series of addition, dissolution and mixing steps.

Table 12 summarises and compares the order of addition of raw materials per the original formulation manufacturing process and the proposed manufacturing process, with a rationale for the change (where applicable). The primary change is to add adrenaline bitartrate in the last step, so that it is introduced into the solution when it already contains buffer, EDTA, and sodium metabisumphite and it has been adjusted to the target pH (all of which act to stabilise adrenaline).

TABLE 12

Order of Addition in Original Formulation and Proposed Manufacturing Processes.

| Step | Original Formulation Manufacturing Process | Proposed Manufacturing Process | Rationale for Change |
|---|---|---|---|
| 1 | Water, cetrimide (1), 2-Hydroxyethyl Cellulose | Purified water | Addition of 2-hydroxyethyl cellulose and cetrimide moved to steps 7 and 8, respectively, so that lignocaine $HCl•H_2O$ and bupivacaine $HCl•H_2O$ are added into a less viscous solution. |

TABLE 12-continued

Order of Addition in Original Formulation and Proposed Manufacturing Processes.

| Step | Original Formulation Manufacturing Process | Proposed Manufacturing Process | Rationale for Change |
|---|---|---|---|
| 2 | Water | Citric acid (Anhydrous)* | Introduces new excipient. Added first to assist dissolution of lignocaine HCl and bupivacaine HCl through lower pH. |
| 3 | Lignocaine HCl•$H_2O$ | Sorbitol | Sorbitol added earlier to assist dissolution of lignocaine HCl•$H_2O$ and bupivacaine HCl•$H_2O$ |
| 4 | Bupivacaine HCl•$H_2O$ | Bupivacaine HCl•$H_2O$ | |
| 5 | Sodium Metabisulphite | Lignocaine HCl•$H_2O$ | Sodium metabisulphite added later to minimise degradation during manufacture |
| 6 | Cetrimide (2) | di-Sodium Edetate (EDTA)* | Introduces new excipient. |
| 7 | Adrenaline Bitartrate, Water | 2-Hydroxyethyl cellulose | 2-Hydroxyethyl cellulose and cetrimide added later to assist dissolution of |
| 8 | Liquid Sorbitol | Cetrimide | Bupivacaine HCl•$H_2O$ and lignocaine HCl•$H_2O$ (mixing into a less viscous solution) |
| 9 | Brilliant Blue, Water | Brilliant Blue | |
| 10 | Water (q.s.) | Sodium Metabisulphite | Sodium metabisulphite added later to minimise degradation during manufacture |
| 11 | | 30% Sulphuric Acid* or 2M NaOH* | Introduces new excipient |
| 12 | | Adrenaline Bitartrate | Adrenaline changed to be added last, so that its degradation is minimised by the presence of excipients which control pH, metal ions and oxidation. |
| 13 | | Purified water (q.s.) | |

*These formulation components are not present in the original formulation.

The changes to the order of manufacturing steps include changes to the introduction of 2-hydroxyethyl cellulose. In the original formulation, this excipient is heated and dissolved in water with a portion of cetrimide in the first manufacturing step, before being mixed and further diluted with water. In the proposed formulation, 2-hydroxyethyl cellulose is added in the $7^{th}$ step (Table 12). 2-Hydroxyethyl cellulose is vulnerable to forming lumps when added to solution and therefore the development of the manufacturing process has introduced manufacturing instructions to ensure addition and mixing conditions result in complete dissolution of this excipient.

In addition to the above changes, development of the manufacturing process also included investigation of holding time and the impact of nitrogen padding (as strategies to reduce oxidative degradation of adrenaline during the manufacturing process).

Stability of Adrenaline Relative to the Original Formulation

Figure 2:
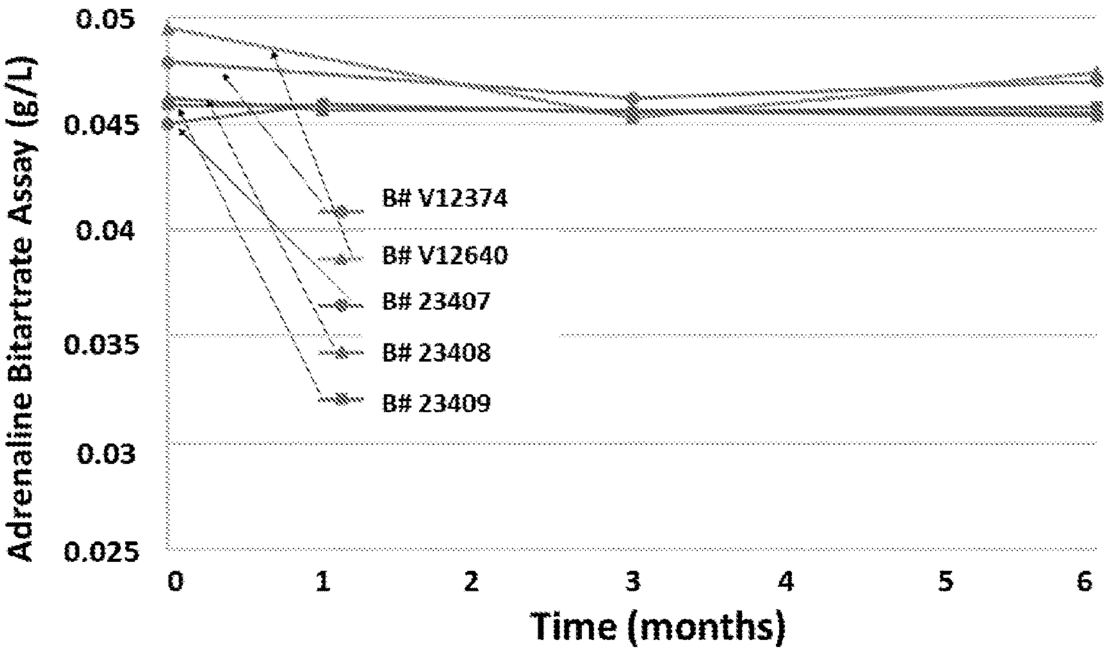
FIG. 2. Adrenaline assay on long term stability—original formulation vs engineering batches (packed batches).
Figure 3:
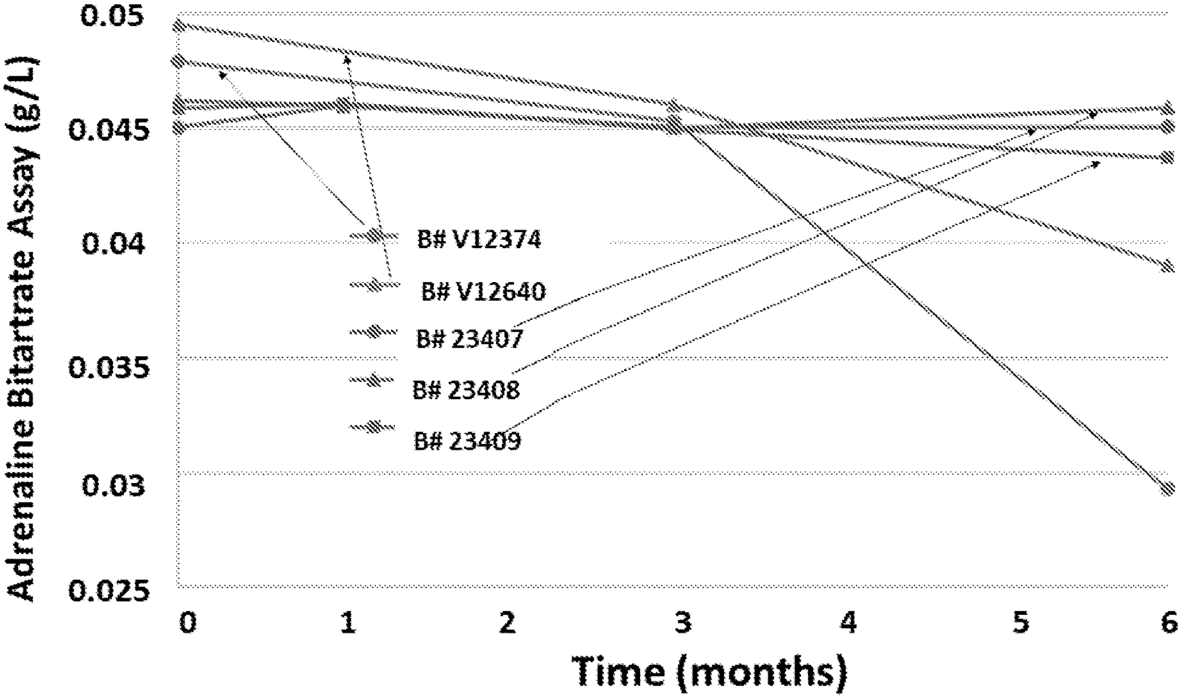
FIG. 3. Adrenaline assay on accelerated stability—original formulation vs engineering batches (packed batches).

FIG. 2 and FIG. 3 compare the adrenaline bitartrate assay of the original formulation with three packed batches of engineering bulk B #23460, under long term and accelerated conditions, respectively. Note that the original formulation is manufactured with a 10% overage of adrenaline and, consequently, the time zero assay is consistently higher for the original formulation relative to the engineering batch (which is not manufactured with an overage).

Under long term conditions, the adrenaline assay shows no consistent trend of decrease with time, for both formulations. However, under accelerated conditions, different trends in the adrenaline assay are evident; a clear and consistent decrease in adrenaline assay with time is observed for the original formulation whereas the adrenaline assay only shows low level variability (broadly consistent with analytical variation) in the engineering batches. The maximum decrease in adrenaline assay for the original formulation was 39%, which is nearly 8 times greater than the maximum decrease in adrenaline assay of 4.7% observed in the engineering batches (B #23409). The available data supports that adrenaline stability is significantly improved in the proposed formulation, relative to the original formulation.

Viscosity Changes Relative to the Original Formulation

Figure 4:
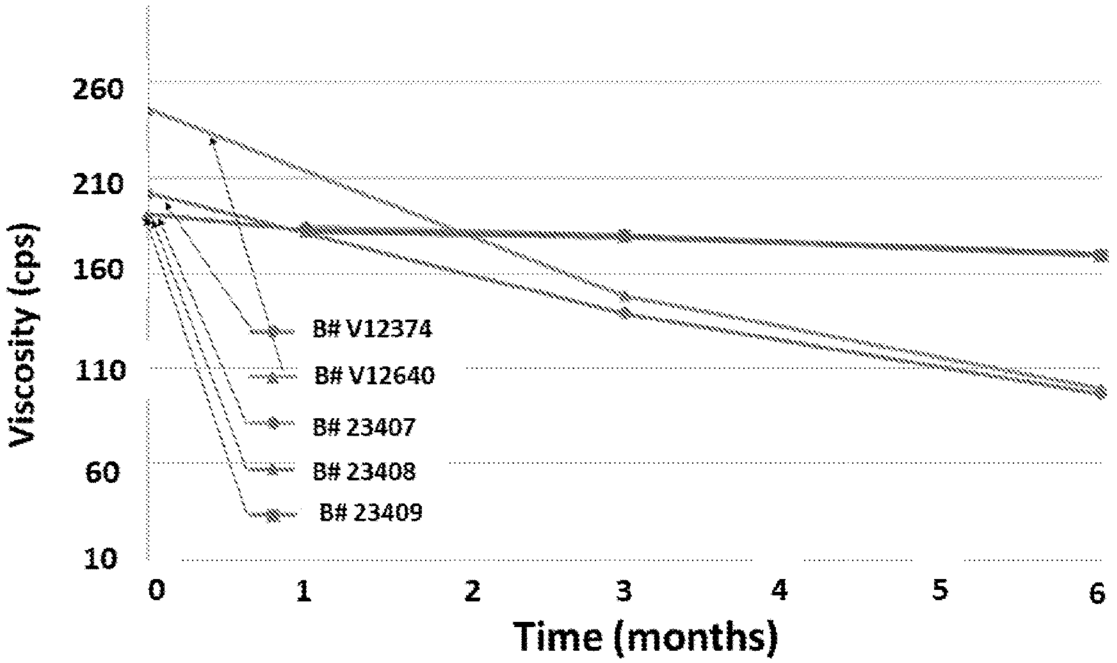
FIG. 4. Viscosity on long term stability—original formulation vs engineering batches (packed batches).
Figure 5:
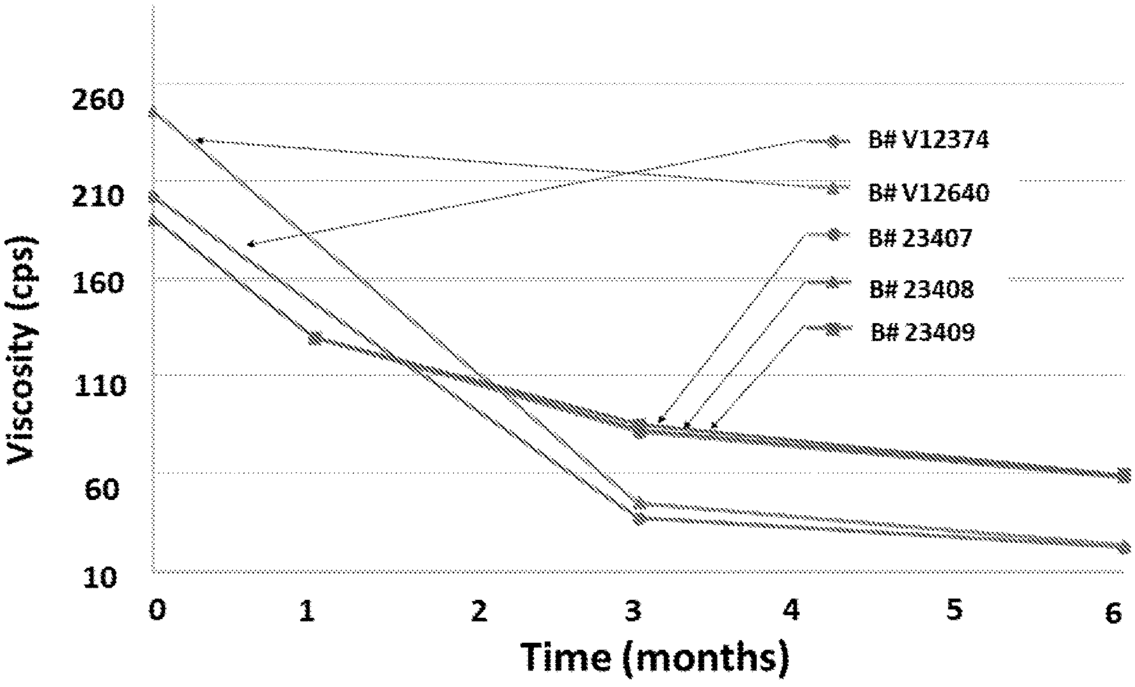
FIG. 5. Viscosity on accelerated stability—original formulation vs engineering batches (packed batches).

FIGS. 4 and 5 compare the original formulation with three packed batches of engineering bulk B #23409, under long term and accelerated conditions, respectively. Note that that time zero viscosity measurements for packed B #s 23407 and 23409 were conducted with a different method, and consequently, time zero viscosity results are not plotted for this batch.

Under both long term and accelerated conditions, a larger change in viscosity is observed for the original formulation relative to the engineering batch. This trend is more apparent under long term conditions, where a clear decrease in viscosity is observed in the original formulation, whereas the viscosity is almost constant in the proposed formulation. Under accelerated conditions, a clear decrease in viscosity with time is observed for both formulations, however the range of change is smaller for the proposed formulation, relative to the original formulation. The available data supports that viscosity changes are reduced in the proposed formulation, relative to the original formulation.

Evaluation of Stability Data

A significant change was observed in the adrenaline assay at the 6 month time point, and consequently, the shelf-life is based on long term stability data. A more detailed discussion of accelerated and long term data follows, below.

Accelerated Conditions

Data from five time points (time zero, one, two, three and six months) is available under accelerated conditions and assessment of trends is possible. Drug substance assay values for lignocaine, bupivacaine and cetrimide are tightly clustered around the time zero value and a linear correlation with valid "goodness of fit ($R^2$)" was not obtained, consistent with the lack of trend in the assay data. In contrast, a significant change (i.e. a 5% change in assay from its initial value was observed at the 6 month time point for both 5 L and 500 mL bottle sizes (Table 13). It is noted that analytical variability is strongly implicated as having a role in the significant change in B #23513, because this is to higher assay value (which is out of trend with other stability data and inconsistent with adrenaline degradation as the cause of the assay change). Observing a significant change in the drug product at the 6 month time point means that the shelf life is based on long term data.

TABLE 13

| Adrenaline Tartrate Assay (g/L), Accelerated Conditions (40° C./75% R.H). | | | | | | | | | | |
|---|---|---|---|---|---|---|---|---|---|---|
| Bulk | | | 1 Month | | 2 Months | | 3 Months | | 6 Months | |
| Batch Number | Packaging | Time 0 | Assay | % Change wrt T = 0 | Assay | % Change wrt T = 0 | Assay | % Change wrt T = 0 | Assay | % Change wrt T = 0 |
| 23513 | 5 L HDPE | 0.0451 | 0.0448 | −0.7 | 0.0453 | 0.4 | 0.0449 | −0.4 | 0.0439 | −2.7 |
| 23514 | Horizontal | 0.0460 | 0.0455 | −1.1 | 0.0454 | −1.3 | 0.0453 | −1.5 | 0.0433 | −5.9 |
| 23515 | | 0.0450 | 0.0451 | 0.2 | 0.0447 | −0.7 | 0.0450 | 0.0 | 0.0433 | −3.8 |
| 23513 | 500 mL | 0.0451 | 0.0448 | −0.7 | 0.0450 | −0.2 | 0.0453 | 0.4 | 0.0473 | 4.9 |
| 23514 | HDPE | 0.0460 | 0.0457 | −0.7 | 0.0456 | −0.9 | 0.0453 | −1.5 | 0.0445 | −3.3 |
| 23515 | Inverted | 0.0450 | 0.0452 | 0.4 | 0.0447 | −0.7 | 0.0433 | −3.8 | 0.0435 | −3.3 |

The decrease in adrenaline assay under accelerated conditions is consistent with the adrenaline assay being shelf-life determining for the original formulation, and also with identification of adrenaline stability as a CQA of the drug product.

Degradation products of lignocaine, bupivacaine and cetrimide were consistently below the limit of quantitation (LOQ). Adrenaline sulfonate was detected in all batches at 6 months, forming at a maximum level of 0.9% (Bulk B #23515, 5 L bottle), complying with the 1.0% limit. Levels of d-adrenaline also increased on stability (Table 14), forming at a maximum level of 14.2% at 6 months (bulk B #23514, 5 L bottle). D-adrenaline is reported for information only.

TABLE 14

| D-Adrenaline (%), Accelerated Conditions (40 °C/75% R.H). | | | | | | |
|---|---|---|---|---|---|---|
| Bulk Batch Number | Packaging | Time 0 | 1 Month | 2 Months | 3 Months | 6 Months |
| 23513 | 5 L HDPE | ND | ND | 10.3 | 13.1 | 13.6 |
| 23514 | Horizontal | ND | ND | 9.7 | 15.0 | 14.2 |

TABLE 14-continued

| D-Adrenaline (%), Accelerated Conditions (40 °C/75% R.H). | | | | | | |
|---|---|---|---|---|---|---|
| Bulk Batch Number | Packaging | Time 0 | 1 Month | 2 Months | 3 Months | 6 Months |
| 23515 | | ND | ND | 9.3 | 12.7 | 13.5 |
| 23513 | 500 mL | ND | ND | 9.1 | 8.7 | 13.6 |
| 23514 | HDPE | ND | ND | 10.2 | 14.3 | 13.9 |
| 23515 | Inverted | ND | ND | 11.5 | 12.9 | 13.1 |

A decrease in sodium metabisulphite assay was also clearly evident under accelerated conditions (Table 15), consistent with its role as a sacrificial antioxidant. The decrease in sodium metabisulphite appears to be greater in the 500 mL bottle size than the 5 L bottle size (with average levels dropping ≈70% and ≈30% at 6 months, respectively), consistent with the larger headspace ratio for the 500 mL bottle (data not shown). Sodium metabisulphite assay is reported for information only, as adrenaline assay and degradation products are the CQA which demonstrate acceptable antioxidant function.

TABLE 15

| Sodium Metabisulfite Assay (g/L), Accelerated Conditions (40 °C/75% R.H). | | | | | | | |
|---|---|---|---|---|---|---|---|
| Bulk Batch Number | Packaging | Time 0 | 1 Month | 2 Months | 3 Months | 6 Months | % Change wrt T = 0 |
| 23513 | 5 L HDPE | 0.0396 | 0.035 | 0.0288 | 0.0307 | 0.0265 | −33.1 |
| 23514 | Horizontal | 0.0402 | 0.0349 | 0.0298 | 0.0316 | 0.0276 | −31.3 |
| 23515 | | 0.0388 | 0.0351 | 0.0299 | 0.0317 | 0.0279 | −28.1 |
| 23513 | 500 mL | 0.0396 | 0.0304 | 0.012 | 0.0151 | 0.012 | −69.7 |
| 23514 | HDPE | 0.0402 | 0.0316 | 0.0135 | 0.0213 | 0.013 | −67.7 |
| 23515 | Inverted | 0.0388 | 0.0318 | 0.0132 | 0.0186 | 0.0131 | −66.2 |

A decrease in viscosity is evident with time and is consistently observed for all batches in both pack sizes (Table 16). Viscosity is not a drug product CQA, the decrease in viscosity is expected and the test result is reported for information only, and consequently, the viscosity decrease is not shelf-life determining. All other physical properties (appearance, pH, specific gravity) showed no trends with time and remained within specifications.

TABLE 16

Viscosity (cps), Accelerated Conditions (40 °C/75% R.H).

| Bulk Batch Number | Packaging | Time 0 | 1 Month | 2 Months | 3 Months | 6 Months | % Change wrt T = 0 |
|---|---|---|---|---|---|---|---|
| 23513 | 5 L HDPE | 199 | 137 | 103 | 78 | 60 | −69.8 |
| 23514 | Horizontal | 204 | 135 | 99 | 79 | 63 | −69.1 |
| 23515 | | 202 | 138 | 96 | 84 | 54 | −73.3 |
| 23513 | 500 mL | 199 | 135 | 101 | 84 | 64 | −67.8 |

TABLE 16-continued

Viscosity (cps), Accelerated Conditions (40 °C/75% R.H).

| Bulk Batch Number | Packaging | Time 0 | 1 Month | 2 Months | 3 Months | 6 Months | % Change wrt T = 0 |
|---|---|---|---|---|---|---|---|
| 23514 | HDPE | 204 | 136 | 101 | 83 | 57 | −72.1 |
| 23515 | Inverted | 202 | 139 | 105 | 86 | 59 | −70.8 |

Long Term Conditions

Data from six time points (time zero, three, six, nine, twelve and eighteen months) is available under long term conditions. All tests remain well within specification and no significant changes have been observed in drug substance assays or drug substance degradation products. The largest change in adrenaline assay, under long term conditions, is 3.9% (observed for bulk B #23514 in the 500 mL bottle size at 3 months 30° C./75% R.H., Table 17). Degradation of adrenaline is not implicated as being the sole cause of this decrease because adrenaline degradation would continue to generate greater decreases in adrenaline assay at subsequent time points and this is not observed. Analytical variability, therefore, is implicated as contributing to this assay change.

TABLE 17

Adrenaline Tartrate (g/L) Assay, Long Term Conditions (25 °C/60% R.H. and 30 °C/75% R.H.).

| | | | 3 Months | | 6 Months | | 9 Months | | 12 Months | | 18 Months | |
|---|---|---|---|---|---|---|---|---|---|---|---|---|
| Bulk Batch Number | Packaging | Time 0 | Assay | % Change wrt T = 0 | Assay | % Change wrt T = 0 | Assay | % Change wrt T = 0 | Assay | % Change wrt T = 0 | Assay | % Change wrt T = 0 |
| 25 °C/60% R.H | | | | | | | | | | | | |
| 23513 | 5 L HDPE | 0.0451 | 0.0454 | 0.7 | 0.0434 | −3.8 | 0.0449 | −0.4 | 0.0459 | 1.8 | 0.0449 | −0.4 |
| 23514 | Horizontal | 0.0460 | 0.0461 | 0.2 | 0.0451 | −2.0 | 0.0452 | −1.7 | 0.0461 | 0.2 | 0.0453 | −0.2 |
| 23515 | | 0.0450 | 0.0452 | 0.4 | 0.0444 | −1.3 | 0.0446 | −0.9 | 0.0455 | 1.1 | 0.0447 | −0.7 |
| 23513 | 500 mL | 0.0451 | 0.0454 | 0.7 | 0.0434 | −3.8 | 0.0447 | −0.9 | 0.0456 | 1.1 | 0.0447 | −0.9 |
| 23514 | HDPE | 0.0460 | 0.0461 | 0.2 | 0.0454 | −1.3 | 0.0453 | −1.5 | 0.0466 | 1.3 | 0.0453 | −1.5 |
| 23515 | Inverted | 0.0450 | 0.0443 | −1.6 | 0.0442 | −1.8 | 0.0445 | −1.1 | 0.0458 | 1.8 | 0.045 | 0.0 |
| 30 °C/75% R.H | | | | | | | | | | | | |
| 23513 | 5 L HDPE | 0.0451 | 0.0453 | 0.4 | 0.0448 | −0.7 | 0.0443 | −1.8 | 0.0450 | −0.2 | 0.0442 | −2.0 |
| 23514 | Horizontal | 0.0460 | 0.0460 | 0.0 | 0.0453 | −1.5 | 0.0449 | −2.4 | 0.0459 | −0.2 | 0.0453 | −1.5 |
| 23515 | | 0.0450 | 0.0448 | −0.4 | 0.0445 | −1.1 | 0.0443 | −1.6 | 0.0450 | 0.0 | 0.0443 | −1.6 |
| 23513 | 500 mL | 0.0451 | 0.0449 | −0.4 | 0.0448 | −0.7 | 0.0446 | −1.1 | 0.0453 | 0.4 | 0.0443 | −1.8 |
| 23514 | HDPE | 0.0460 | 0.0442 | −3.9 | 0.0449 | −2.4 | 0.0449 | −2.4 | 0.0464 | 0.9 | 0.0452 | −1.7 |
| 23515 | Inverted | 0.0450 | 0.0453 | 0.7 | 0.0442 | −1.8 | 0.0442 | −1.8 | 0.0451 | 0.2 | 0.0442 | −1.8 |

Figure 6:
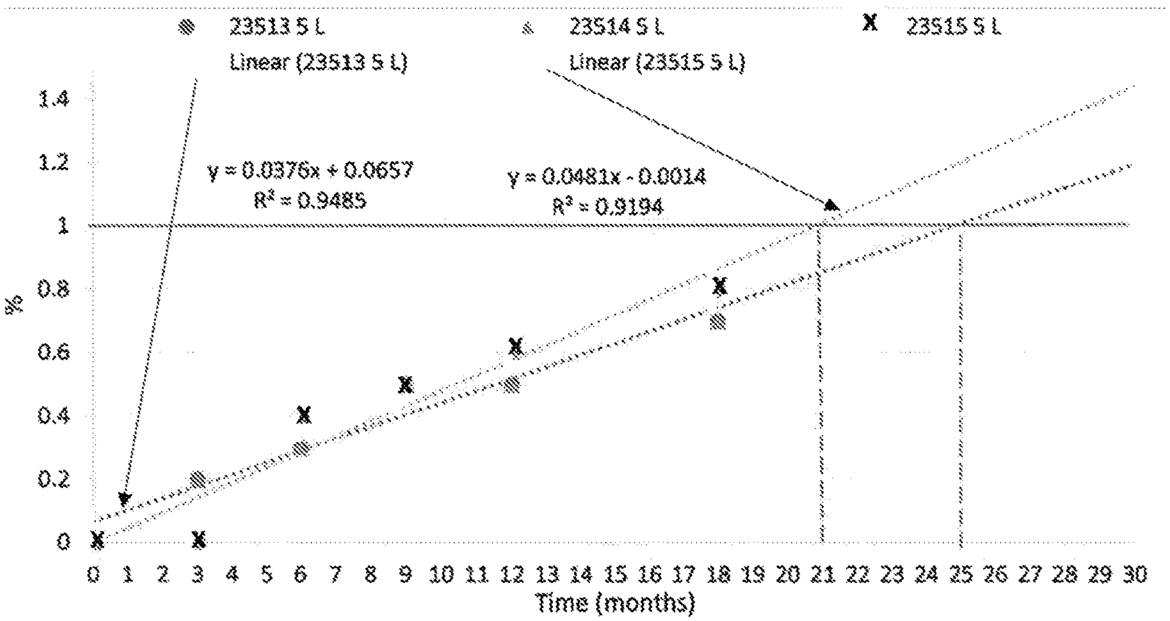
FIG. 6. Adrenaline sulphonate and its linear regression for engineering batches packed in 5 L HDPE stored at 30° C./75% R.H., batches 23513 and 23514 have the same plot and linear regression.
Figure 7:
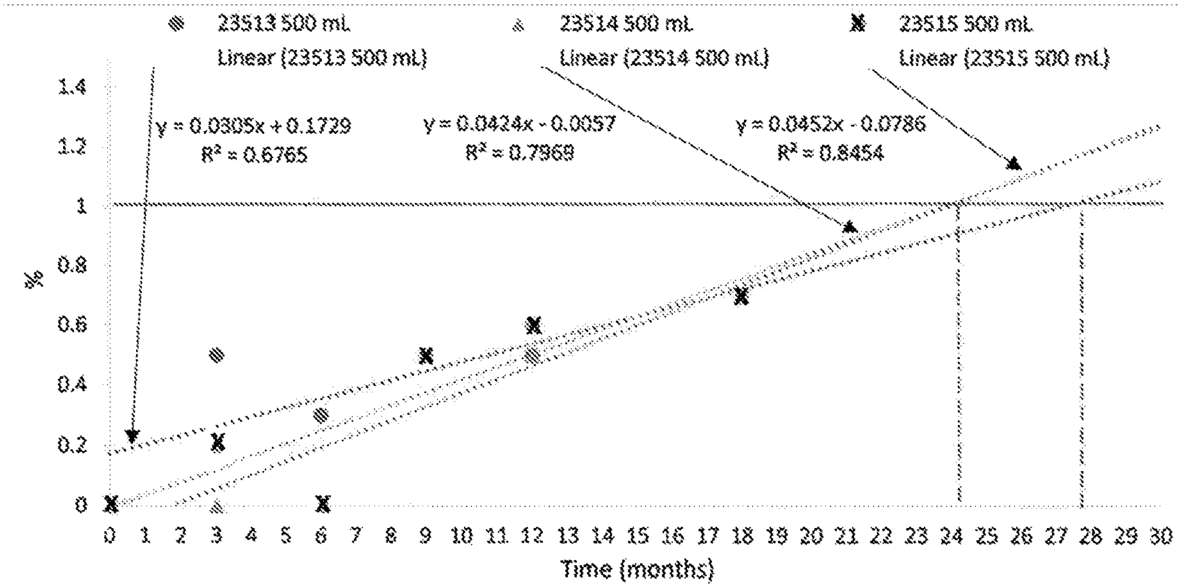
FIG. 7. Adrenaline sulphonate and its linear regression for engineering batches packed in 500 mL HDPE stored at 30° C./75% R.H.

The maximum level of adrenaline sulfonate, under long term conditions, is 0.8% (80% of the 1.0% specification, 18 months, B #23515, 5 L bottle, 30° C./75% R.H., Table 18) indicating that formation of adrenaline sulphonate may be shelf life determining (consistent with accelerated data). Linear regression of the levels of adrenaline sulfonate was performed for product stored at 30° C./75% R.H. in 5 L HDPE and 500 mL HDPE (FIGS. 6 and 7), it was found that the predicted shelf-life based on adrenaline tartrate is 24 months and 25 months, respectively. There is insufficient data to perform linear regression to predict the shelf-life for product stored at 25° C./60% R.H., as adrenaline sulphonate was detected on only two samples at the 3 month time point and all subsequent samples. However, from the level of adrenaline sulfonate as shown in Table 18, it is evident that the shelf-life for product stored at 25° C./60% R.H. will be at least 24 months. It is noted that this estimate is likely to be conservative because sulphonation reaction rates are anticipated to slow with time as the sodium metabisulphite level in the drug product decreases with time (Table 20). Levels of d-adrenaline also increased, ranging from 12.6% to 13.1% and 7.0% to 8.5% at 18 months, 30° C./75% R.H. and 25° C./60% R.H., respectively (Table 19). d-Adrenaline is reported for information only and, consequently, the formation of the alternate stereoisomer is not shelf-life determining.

TABLE 18

Adrenaline Sulfonate (%), Long Term Conditions (25 °C/60% R.H. and 30 °C/75% R.H.).

| Bulk Batch Number | Packaging | Time 0 | 3 Months | 6 Months | 9 Months | 12 Months | 18 Months |
|---|---|---|---|---|---|---|---|
| 25 °C/60% R.H. | | | | | | | |
| 23513 | 5 L HDPE | ND | ND | ND | 0.3 | 0.3 | 0.4 |
| 23514 | Horizontal | ND | 0.2 | ND | 0.3 | 0.3 | 0.4 |
| 23515 | | ND | ND | ND | 0.3 | 0.3 | 0.4 |
| 23513 | 500 mL | ND | 0.2 | ND | 0.3 | 0.3 | 0.4 |
| 23514 | HDPE | ND | ND | ND | 0.3 | 0.3 | 0.4 |
| 23515 | Inverted | ND | ND | ND | 0.3 | 0.3 | 0.4 |
| 30 °C/75% R.H. | | | | | | | |
| 23513 | 5 L HDPE | ND | 0.2 | 0.3 | 0.5 | 0.5 | 0.7 |
| 23514 | Horizontal | ND | 0.2 | 0.3 | 0.5 | 0.5 | 0.7 |
| 23515 | | ND | ND | 0.4 | 0.5 | 0.6 | 0.8 |
| 23513 | 500 mL | ND | 0.5 | 0.3 | 0.5 | 0.5 | 0.7 |
| 23514 | HDPE | ND | ND | ND | 0.5 | 0.5 | 0.7 |
| 23515 | Inverted | ND | 0.2 | ND | 0.5 | 0.6 | 0.7 |

TABLE 19

D-Adrenaline (%), Long Term Conditions (25 °C/60% R.H. and 30 °C/75% R.H.).

| Bulk Batch Number | Packaging | Time 0 | 3 Months | 6 Months | 9 Months | 12 Months | 18 Months |
|---|---|---|---|---|---|---|---|
| 25 °C/60% R.H. | | | | | | | |
| 23513 | 5 L HDPE | ND | ND | ND | 2.8 | 8.5 | 6.6 |
| 23514 | Horizontal | ND | ND | ND | 3.2 | 7.6 | 6.3 |
| 23515 | | ND | ND | ND | 2.6 | 7.0 | 6.0 |
| 23513 | 500 mL | ND | ND | ND | 3.2 | 7.6 | 6.1 |
| 23514 | HDPE | ND | ND | ND | 3.2 | 7.5 | 7.5 |
| 23515 | Inverted | ND | ND | ND | 3.0 | 7.6 | 6.9 |
| 30 °C/75% R.H. | | | | | | | |
| 23513 | 5 L HDPE | ND | 7.3 | 4.3 | 5.5 | 12.2 | 12.6 |
| 23514 | Horizontal | ND | ND | 3.9 | 5.9 | 12.9 | 13.0 |
| 23515 | | ND | 7.4 | 3.8 | 5.3 | 12.0 | 12.6 |
| 23513 | 500 mL | ND | 16.0 | 4.4 | 6.1 | 12.3 | 12.9 |
| 23514 | HDPE | ND | 7.2 | 3.8 | 6.1 | 13.0 | 13.1 |
| 23515 | Inverted | ND | ND | 2.8 | 5.3 | 12.3 | 12.8 |

A decrease in sodium metabisulphite assay was also clearly evident under long term conditions, consistent with accelerated data and with its role as a sacrificial antioxidant. The decrease in sodium metabisulphite is greater in the 500 mL bottle size than the 5 L bottle size, consistent with accelerated data and the larger headspace ratio for the 500 mL bottle (data not shown). Sodium metabisulphite assay is reported for information only, as adrenaline assay and degradation products are the CQA which demonstrate acceptable antioxidant function. Consequently, the decrease in sodium metabisulfite is not shelf-life determining.

TABLE 20

Sodium Metabisulfite (g/L), Long Term Conditions (25 °C/60% R.H. and 30 °C/75% R.H.).

| Bulk Batch Number | Packaging (Head Space Ratio) | Time 0 | 3 Months | 6 Months | 9 Months | 12 Months | 18 Months | % change wrt T = 0 |
|---|---|---|---|---|---|---|---|---|
| 25 °C/60% R.H. | | | | | | | | |
| 23513 | 5 L HDPE | 0.0396 | 0.0330 | 0.0323 | 0.0327 | 0.0333 | 0.0325 | −17.9 |
| 23514 | Horizontal | 0.0402 | 0.0350 | 0.0333 | 0.0332 | 0.0332 | 0.0341 | −15.2 |
| 23515 | (1:4.0) | 0.0388 | 0.0368 | 0.0340 | 0.0344 | 0.0344 | 0.0389 | 0.3 |
| 23513 | 500 mL | 0.0396 | 0.0208 | 0.0173 | 0.0161 | 0.0207 | 0.0157 | −60.1 |
| 23514 | HDPE | 0.0402 | 0.0213 | 0.0187 | 0.0170 | 0.0198 | 0.0165 | −59.0 |
| 23515 | Inverted (1:9.3) | 0.0388 | 0.0232 | 0.0189 | 0.0189 | 0.0211 | 0.0196 | −49.5 |
| 30 °C/75% R.H. | | | | | | | | |
| 23513 | 5 L HDPE | 0.0396 | 0.0342 | 0.0311 | 0.0313 | 0.0311 | 0.0324 | −18.2 |
| 23514 | Horizontal | 0.0402 | 0.0346 | 0.0323 | 0.0327 | 0.0315 | 0.0379 | −5.7 |
| 23515 | (1:4.0) | 0.0388 | 0.0353 | 0.0328 | 0.0328 | 0.0324 | 0.0379 | −2.3 |

TABLE 20-continued

| Sodium Metabisulfite (g/L), Long Term Conditions (25 °C/60% R.H. and 30 °C/75% R.H.). | | | | | | | | |
|---|---|---|---|---|---|---|---|---|
| Bulk Batch Number | Packaging (Head Space Ratio) | Time 0 | 3 Months | 6 Months | 9 Months | 12 Months | 18 Months | % change wrt T = 0 |
| 23513 | 500 mL | 0.0396 | 0.0175 | 0.0173 | 0.0153 | 0.0170 | 0.0117 | −70.5 |
| 23514 | HDPE | 0.0402 | 0.0214 | 0.0179 | 0.0153 | 0.0173 | 0.0177 | −56.0 |
| 23515 | Inverted (1:9.3) | 0.0388 | 0.0212 | 0.0188 | 0.0161 | 0.0187 | 0.0203 | −47.7 |

A decrease in viscosity was evident with time and is consistently observed for all batches in both pack sizes. Viscosity is not a drug product CQA, the decrease in viscosity is expected and the test result is reported for information only and, consequently, the viscosity decrease is not shelf-life determining. All other physical properties (appearance, pH, specific gravity) showed no trends with time and remained within specifications.

TABLE 21

| Viscosity (cps), Long Term Conditions (25 °C/60% R.H. and 30 °C/75% R.H.). | | | | | | | | | |
|---|---|---|---|---|---|---|---|---|---|
| Bulk Batch Number | Packaging | Time 0 | 3 Months | 6 Months | 9 Months | 12 Months | 18 Months | Change (abs) | Change (%) |
| 25 °C/60% R.H. | | | | | | | | | |
| 23513 | 5 L HDPE | 199 | 181 | 176 | 153 | 150 | 138 | 61 | 31 |
| 23514 | Horizontal | 204 | 188 | 171 | 158 | 150 | 137 | 67 | 33 |
| 23515 | (1:4.0) | 202 | 190 | 175 | 161 | 161 | 139 | 63 | 31 |
| 23513 | 500 mL | 199 | 186 | 177 | 156 | 150 | 133 | 66 | 33 |
| 23514 | HDPE | 204 | 190 | 175 | 156 | 148 | 129 | 75 | 37 |
| 23515 | Inverted (1:9.3) | 202 | 186 | 175 | 163 | 151 | 131 | 71 | 35 |
| 30 °C/75% R.H. | | | | | | | | | |
| 23513 | 5 L HDPE | 199 | 156 | 138 | 117 | 106 | 85 | 114 | 57 |
| 23514 | Horizontal | 204 | 163 | 138 | 115 | 105 | 82 | 122 | 60 |
| 23515 | (1:4.0) | 202 | 179 | 140 | 118 | 107 | 87 | 115 | 57 |
| 23513 | 500 mL | 199 | 169 | 139 | 116 | 105 | 89 | 110 | 55 |
| 23514 | HDPE | 204 | 164 | 139 | 116 | 109 | 86 | 118 | 58 |
| 23515 | Inverted (1:9.3) | 202 | 168 | 141 | 119 | 106 | 85 | 117 | 58 |

It is noted that there was a four month delay between manufacture of the VICH batches and placement on stability. Consequently, the current 18 month stability time point corresponds to 22 months after manufacture. The current long term stability data, therefore, indicates that the drug product remains well within specification on 22 months storage under ambient conditions.

CONCLUSIONS

The significant decrease (−5.9% and 4.9%) in adrenaline assay at 6 months under accelerated conditions precludes assigning a shelf life based on accelerated data, and long term data is available to propose a shelf-life of the product. The data indicates that the drug product remains well within specification with 18 months, and based on the linear regression of adrenaline sulfonate performed for product stored at 30° C./75% R.H. (FIGS. 6 and 7), the shelf-life of the product may be at least 24 months. This assessment of potential shelf-life is potentially conservative because (1) it is based on a linear relationship between the impurity growth and time, and sulphonation reactions rates are anticipated to slow with time as the sodium metabisulphite level in the drug product decreases, and (2) the drug product was stored for 4 months, under ambient conditions, before placement on stability.

Example 4—Formulation of a Topical Anaesthetic Gel

This example describes the preparation of a topical anaesthetic composition, based on findings in the earlier Examples, in the form of a spray-on gel. The composition has the following formulation:

5% w/w lignocaine hydrochloride;
0.5% w/w bupivacaine hydrochloride;
0.5% w/w cetrimide;
0.0045% w/w adrenaline bitartrate;
10% w/w liquid sorbitol (70%);
0.5% w/w 2-hydroxyethyl cellulose;
0.0045% w/w sodium metabisulfite;
0.250% w/w citric acid (anhydrous);
0.05% w/w disodium EDTA;

optionally, a pH adjuster, with a quantity to suit; and water, with a quantity to suit, wherein said composition has a final pH of about 2.9.

The composition is prepared in the manner described below. These ingredients are added in the following order:

1. Water;
2. Citric acid;
3. Sorbitol;
4. Bupivacaine and/or lignocaine;
5. EDTA;
6.2-Hydroxyethyl cellulose;
7. Cetrimide
8. Detectable marker (if any);
9. Sodium metabisulphite;
10. pH adjuster (if required);
11. Adrenaline; and
12. Water, to balance.

The composition has a final pH of 2.9.

Example 5—Use of a Topical Anaesthetic Composition in Mulesing

This example describes the use of the composition of Example 4 in mulesing.

If necessary, the breech area of the sheep is crutched of wool. Mulesing is then performed. This involves removing strips of skin from either side of the perineum and from the dorsal surface of the tail. The tail may be docked at the same time. The composition is then immediately applied to the surgical wound as a coloured gel by a metered dose spray-on pump pack or trigger spray bottle. About 5-15 mLs of the composition is applied, depending on the size of the wound and the animal.

Example 6—Use of a Topical Anaesthetic Composition for Castration

This example describes the use of the composition of Example 4 for animal castration.

The animal should be held firmly and securely in a cradle or restraint designed for routine surgical castration. An incision is made in the scrotal sac and the testes and chordal tissue exposed as per routine surgical castration. The composition is then sprayed onto the chordal tissue so as to fully coat it, particularly at the site of the incision and along the length of chordal tissue that will remain and retract into the scrotal sac after the testes are excised. Depending on the size of the animal, approximately 0.5-2 mLs of spray-on composition is used. The testes are then excised by cutting through the chordal tissue at the level where the composition has been applied, using routine surgical castration technique. The empty scrotal sac and edges of the skin incision are then sprayed with an additional dose of the composition so as to fill the sac and coat the cut skin edges. Depending on the size of the animal, approximately 1-4 mLs of spray-on composition is used.

Example 7—Use of a Topical Anaesthetic Composition for Shearing Cuts, Skin Lacerations and Superficial Burns This example describes the use of the composition of Example 4 for shearing cuts, skin lacerations and superficial burns.

Where a significant skin laceration or superficial (1st or second degree) burn occurs, such as during shearing or branding, or following a misadventure, the composition may be sprayed directly onto the wound so as to coat the wound and cover the cut skin edges. The spray is applied by metered dose. The volume applied will vary depending on the size of the wound and animal. For instance, a total dose of 50 mg/kg of lignocaine should not be exceeded for sheep.

Example 8—Use of a Topical Anaesthetic Composition for Dehorning

This example describes the use of the composition of Example 4 for dehorning.

Where dehorning of animals is carried out leaving a raw, bleeding bed of tissue, the composition may be applied directly to the raw tissue bed immediately following dehorning either by metered spray, or by metered squeeze application of the composition so as to cover the entire exposed tissue bed and remain in contact with it. Estimated volumes required are 1-3 mLs per dehorned tissue bed depending on the size of the wound. The total dose applied should not exceed safety limits of mg/kg lignocaine (topically applied) for the animal species involved.

Additional Data

- Lignocaine hydrochloride: CAS No.: 6108-05-0
- Bupivacaine hydrochloride: CAS No.: 14252-80-3/73360-54-0
- Adrenaline acid tartrate: CAS No.: 51-42-3
- Cetrimide: CAS No.: 8044-71-1
- Sorbitol (humectant): CAS No.: 50-70-4
- 2-hydroxyethyl cellulose (viscosity modifier): CAS No.: 9004-62-0
- Sodium metabisulfite (Antioxidant): CAS No.: 7681-57-4
- Citric acid anhydrous (Buffer): CAS No.: 77-92-9
- Disodium edetate (Chelating agent): CAS No.: 6381-92-6
- Sodium hydroxide (pH adjustor): CAS No.: 1310-73-2
- 30% sulphuric acid (pH adjustor): CAS No.: 7664-93-9
- Brillian blue FCF (Colourant): CAS No.: 3844-45-9
- Purified water (RO) (Diluent): CAS No.: 7732-18-5
- Formulation type: e.g., pour-on, tablet, powder, paste, aerosol, wettable powder, emulsifiable concentrate etc.

Throughout this specification, unless in the context of usage an alternative interpretation is required, the term "comprise" (and variants thereof such as "comprising" and "comprised") denotes the inclusion of a stated integer or integers but does not exclude the presence of another integer or other integers.

It will be appreciated by one of skill in the art that many changes can be made to the composition and uses exemplified above without departing from the broad ambit and scope of the invention.

The invention claimed is:

1. A topical anaesthetic composition comprising in percentage weight/weight (% w/w):

5% w/w ±10% variance of lignocaine salt;

4-0.5% w/w ±10% variance of bupivacaine salt;

0.5% w/w ±10% variance of cetrimide;

0.0045% w/w ±10% variance of adrenaline salt or ester;

10% w/w ±10% variance of liquid sorbitol (70%);

0.5% w/w ±10% variance of 2-hydroxyethyl cellulose;

0.0045% w/w ±10% variance of sodium metabisulfite;

0.250% w/w ±10% variance of citric acid; and 0.05% w/w ±10% variance of EDTA salt, wherein said composition has a final pH of approximately 2.4 to 3.4±10% variance, and the composition has a density in the range of 1.01 to 1.05 g/mL ±10% variance.

2. The composition of claim 1, having one or more properties selected from the group consisting of:
the lignocaine salt is lignocaine hydrochloride;
the bupivacaine salt is bupivacaine hydrochloride;
the adrenaline salt is adrenaline bitartrate;
the EDTA salt is disodium EDTA;
the composition has a pH of 2.9±0.10% variance;
the composition has a pH of 2.9±0.10% variance;
A the composition further comprises a detectable marker;
the composition further comprises a pH adjuster; and
the composition has a viscosity not more than about 300 cP.

3. The composition of claim 1, having a property selected from the group consisting of:
the composition is stable for at least 12 months when stored between about 20° C. and about 30° C.;
the composition is stable for at least 18 months when stored between about 20° C. and about 30° C.; and
the composition is stable for at least 24 months when stored between about 20° C. and about 30° C.

4. The composition of claim 1, having a property selected from the group consisting of:
the composition is semi-viscous;
the composition is in the form of a sticky, viscous gel;
the composition is in the form of a sprayable gel;
the composition is in the form of a gel that can be squeezed or dispensed from a tube; and
the composition is in the form of a spray-on gel that can coat a wound of the subject and can maximise delivery of active ingredients to the wound by way of staying moist, viscous and sticky.

5. The composition of claim 1, comprising in percentage weight/volume (% w/v):
about 5% w/v lignocaine salt;
about 0.5% w/v bupivacaine salt;
about 0.5% w/v cetrimide;
about 0.0045% w/v adrenaline salt or ester;
about 10% w/v liquid sorbitol (70%);
about 0.5% w/v to about 0.6% w/v 2-hydroxyethyl cellulose;
about 0.0045% w/v sodium metabisulfite;
about 0.250% w/v citric acid (anhydrous);
about 0.05% w/v EDTA salt;
A optionally, a detectable marker, with a quantity to suit;
optionally, a pH adjuster, with a quantity to suit; and
water, with a quantity to suit,
wherein said composition has a final pH of about 2.9.

6. The composition of claim 5, comprising:
about 5% w/v lignocaine hydrochloride as the lignocaine salt;
about 0.5% w/v bupivacaine hydrochloride as the bupivacaine salt;
about 0.5% w/v cetrimide;
about 0.0045% w/v adrenaline bitartrate as the adrenaline salt;
about 10% w/v liquid sorbitol (70%);
about 0.5% w/v 2-hydroxyethyl cellulose or about 0.6% w/v 2-hydroxyethyl cellulose;
about 0.0045% w/v sodium metabisulfite;
about 0.250% w/v citric acid (anhydrous);
about 0.05% w/v disodium EDTA as the EDTA salt;
A optionally, a detectable marker, with a quantity to suit;
optionally, a pH adjuster, with a quantity to suit; and
water, with a quantity to suit,
wherein said composition has a final pH of about 2.9.

7. The composition of claim 6, having one or more properties selected from the group consisting of:
the composition has a pH of 2.9±0.10% variance;
A the composition comprises a detectable marker;
the composition comprises a pH adjuster; and
the composition has a viscosity not more than about 300 cP.

8. The composition of claim 6, having a property selected from the group consisting of:
the composition is stable for at least 12 months when stored between about 20° C. and about 30° C.;
the composition is stable for at least 18 months when stored between about 20° C. and about 30° C.; and
the composition is stable for at least 24 months when stored between about 20° C. and about 30° C.

9. The composition of claim 6, having a property selected from the group consisting of:
the composition is semi-viscous;
the composition is in the form of a sticky, viscous gel;
the composition is in the form of a sprayable gel; and
the composition is in the form of a spray-on gel that can coat a wound and can maximise delivery of active ingredients to the wound by way of staying moist, viscous and sticky.

10. A composition comprising in percentage weight/volume (% w/v):
about 5% w/v lignocaine hydrochloride;
about 0.5% w/v bupivacaine hydrochloride;
about 0.5% w/v cetrimide;
about 0.0045% w/v adrenaline bitartrate;
about 0.5% w/v to about 0.6% w/v 2-hydroxyethyl cellulose;
about 0.0045% w/v sodium metabisulfite;
about 10% w/v liquid sorbitol (70%);
about 0.005% w/v colourant, such as a pigment or dye;
about 0.25% w/v citric acid (anhydrous);
about 0.05% w/v disodium EDTA;
optionally, a pH adjuster, with a quantity to suit; and
water, with a quantity to suit,
wherein said composition has a final pH of about 2.9.

11. The composition of claim 10, comprising about 0.5% w/v or about 0.6% w/v 2-hydroxyethyl cellulose.

12. The composition of claim 10, comprising a pH adjuster.

13. The composition of claim 10, wherein the colourant is a pigment or dye.

14. A method of treatment selected from the group consisting of:
anaesthetizing a subject;
anaesthetizing an open wound or a sutured skin wound of a subject;
anaesthetizing a subject undergoing or about to undergo an animal husbandry procedure or surgical procedure;
treating an open wound of a subject such as caused by shearing, misadventure or surgical incision;
treating an open wound of a subject caused by an animal husbandry procedure; and
treating an open wound of a subject caused by mulesing, shearing, castrating, tail docking, ear tagging, ear notching, de-horning, branding or marking,
comprising the step of administering to the subject the composition according to claim 1, wherein the subject is selected from the group consisting of:
a non-human animal;
a mammal;
a farm animal or livestock;
a companion animal;
a laboratory animal;
a dog, pig, piglet, horse, sheep, cow, lamb or calf, and
a human.

15. The method of claim 14, wherein the composition comprises:

about 5% w/v lignocaine salt;
about 0.5% w/v bupivacaine salt;
about 0.5% w/v cetrimide;
about 0.0045% w/v adrenaline salt or ester;
about 10% w/v liquid sorbitol (70%);
about 0.5% w/v to about 0.6% w/v 2-hydroxyethyl cellulose;
about 0.0045% w/v sodium metabisulfite;
about 0.250% w/v citric acid (anhydrous);
about 0.05% w/v EDTA salt;
A optionally, a detectable marker, with a quantity to suit;
optionally, a pH adjuster, with a quantity to suit; and
water, with a quantity to suit,
wherein said composition has a final pH of about 2.9.

16. The method of claim 15, wherein the composition comprises:

about 5% w/v lignocaine hydrochloride;
about 0.5% w/v bupivacaine hydrochloride;
about 0.5% w/v cetrimide;
about 0.0045% w/v adrenaline bitartrate;
about 0.5% w/v to about 0.6% w/v 2-hydroxyethyl cellulose;
about 0.0045% w/v sodium metabisulfite;
about 10% w/v liquid sorbitol (70%);
A about 0.005% w/v colourant;
about 0.25% w/v citric acid (anhydrous);
about 0.05% w/v disodium EDTA;
optionally, a pH adjuster, with a quantity to suit; and
water, with a quantity to suit,
wherein said composition has a final pH of about 2.9.

17. The method of claim 16, wherein the subject is an animal, and the composition comprises:

about 5% w/v lignocaine hydrochloride;
about 0.5% w/v bupivacaine hydrochloride;
about 0.5% w/v cetrimide;
about 0.0045% w/v adrenaline bitartrate;
about 0.5% w/v 2-hydroxyethyl cellulose;
about 0.0045% w/v sodium metabisulfite;
about 10% w/v liquid sorbitol (70%);
about 0.005% w/v colourant;
about 0.25% w/v citric acid (anhydrous);
about 0.05% w/v disodium EDTA;
optionally, a pH adjuster, with a quantity to suit; and
water, with a quantity to suit,
wherein said composition has a final pH of about 2.9.

18. The method of claim 16, wherein the subject is a human, and the composition comprises:

about 5% w/v lignocaine hydrochloride;
about 0.5% w/v bupivacaine hydrochloride;
about 0.5% w/v cetrimide;
about 0.0045% w/v adrenaline bitartrate;
about 0.6% w/v 2-hydroxyethyl cellulose;
about 0.0045% w/v sodium metabisulfite;
about 10% w/v liquid sorbitol (70%);
A about 0.005% w/v colourant;
about 0.25% w/v citric acid (anhydrous);
about 0.05% w/v disodium EDTA;
optionally, a pH adjuster, with a quantity to suit; and
water, with a quantity to suit,
wherein said composition has a final pH of about 2.9.

* * * * *